US009297686B1

(12) United States Patent
Ross, Jr.

(10) Patent No.: US 9,297,686 B1
(45) Date of Patent: Mar. 29, 2016

(54) LIQUID LEVEL TRANSDUCER WITH INSERTABLE QUALITY SENSOR

(71) Applicant: Texas LFP, LLC, Dallas, TX (US)

(72) Inventor: Herbert G. Ross, Jr., Argyle, TX (US)

(73) Assignee: Texas LFP, LLC, Dallas, TX (US)

( * ) Notice: Subject to any disclaimer, the term of this patent is extended or adjusted under 35 U.S.C. 154(b) by 0 days.

(21) Appl. No.: 14/677,914

(22) Filed: Apr. 2, 2015

(51) Int. Cl.
| G01F 23/00 | (2006.01) |
| G01F 23/292 | (2006.01) |
| G01F 23/26 | (2006.01) |
| G01F 23/22 | (2006.01) |
| G01F 23/24 | (2006.01) |
| G01N 27/02 | (2006.01) |
| G01N 33/28 | (2006.01) |

(52) U.S. Cl.
CPC ............ *G01F 23/292* (2013.01); *G01F 23/263* (2013.01); *G01F 23/22* (2013.01); *G01F 23/24* (2013.01); *G01F 23/266* (2013.01); *G01F 23/2922* (2013.01); *G01F 23/2925* (2013.01); *G01N 27/028* (2013.01); *G01N 33/2888* (2013.01)

(58) Field of Classification Search
CPC ... G01F 23/292; G01F 23/22; G01F 23/2922; G01F 23/24; G01F 23/2925; G01F 23/263; G01F 23/266; G01N 27/028; G01N 33/00; G01N 33/2888
USPC ........ 73/290 R, 293, 304 R, 327, 291, 304 C; 250/903
See application file for complete search history.

(56) References Cited

U.S. PATENT DOCUMENTS

| 5,410,913 A | 5/1995 | Blackburn |
| 6,089,086 A | 7/2000 | Swindler et al. |
| 6,250,152 B1* | 6/2001 | Klein et al. ................. 73/304 C |
| 7,013,728 B2 | 3/2006 | Okada et al. |
| 7,043,967 B2* | 5/2006 | Kauffman .............. G01N 33/28 73/295 |
| D625,396 S | 10/2010 | Gismervik |
| 9,021,878 B2* | 5/2015 | Grinstein et al. .......... 73/204.11 |
| 2004/0060344 A1* | 4/2004 | Kauffman .............. G01N 33/28 73/53.01 |
| 2008/0143345 A1 | 6/2008 | Boudaoud et al. |
| 2008/0314141 A1* | 12/2008 | Keith et al. ................. 73/290 R |
| 2009/0007660 A1* | 1/2009 | Van Ee ............................ 73/299 |
| 2009/0260432 A1* | 10/2009 | Olah ........................... 73/290 R |
| 2010/0327884 A1 | 12/2010 | McCall et al. |
| 2011/0000297 A1 | 1/2011 | Ford |
| 2013/0008247 A1* | 1/2013 | Bardsley et al. ................ 73/306 |
| 2013/0068015 A1* | 3/2013 | Sinha et al. ..................... 73/304 |
| 2014/0226149 A1* | 8/2014 | Coates et al. ................... 356/51 |
| 2015/0013646 A1* | 1/2015 | Qi ................................. 123/478 |

FOREIGN PATENT DOCUMENTS

GB      2476317 A    6/2011

* cited by examiner

*Primary Examiner* — Lisa Caputo
*Assistant Examiner* — Jonathan Dunlap
(74) *Attorney, Agent, or Firm* — Alvin R. Wirthlin

(57) ABSTRACT

An apparatus for determining at least first and second properties of a fluid associated with a tank includes a mounting head adapted for connection to the tank, a housing extending from the mounting head, and an integral chamber formed in the housing. The chamber is in fluid communication between the tank and a down-line device of the vehicle or equipment with which the tank is associated. A sensor module can be installed in the chamber for measuring different parameters of the fluid. Other modules can be interchanged with the sensor module for accomplishing different operations associated with the apparatus and/or fluid.

26 Claims, 13 Drawing Sheets

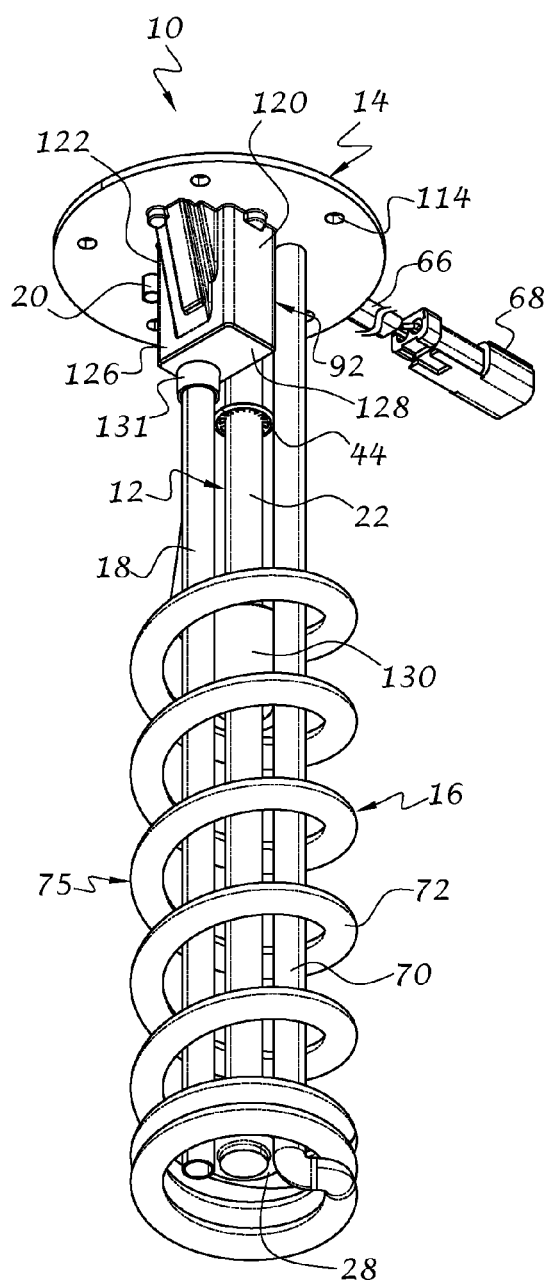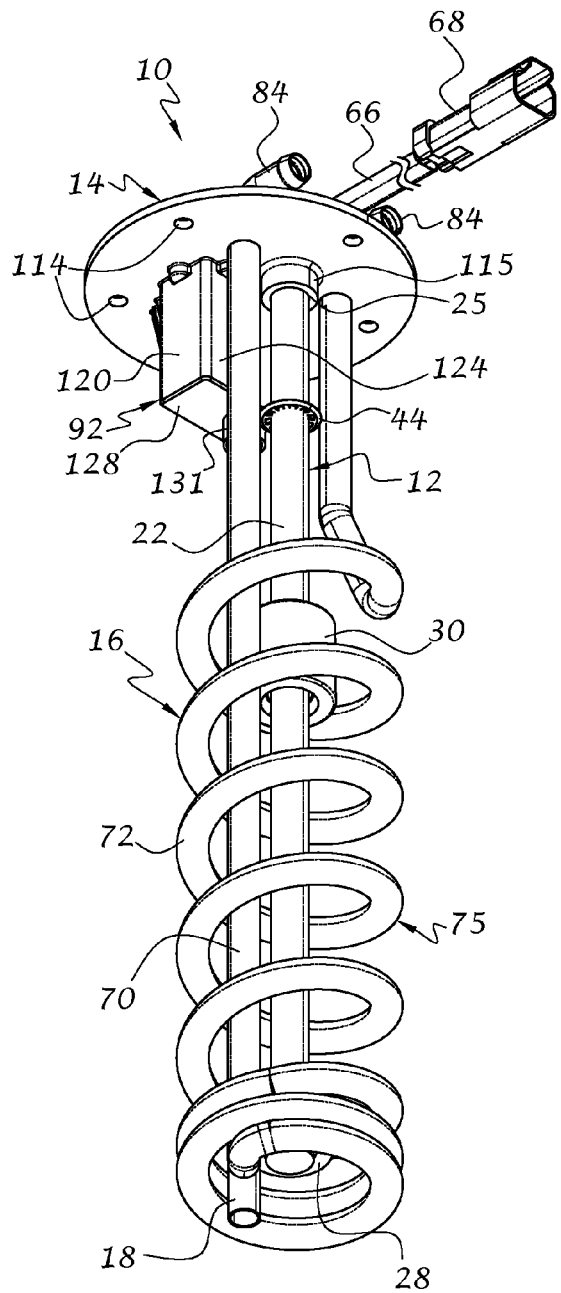
FIG. 3
FIG. 4

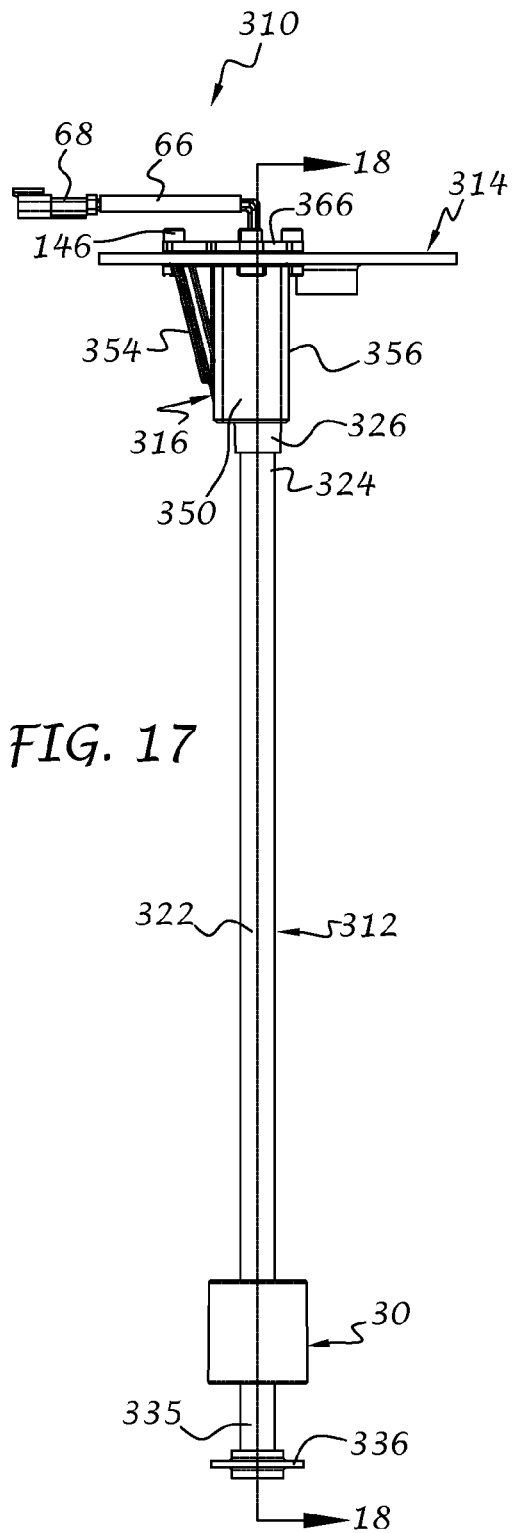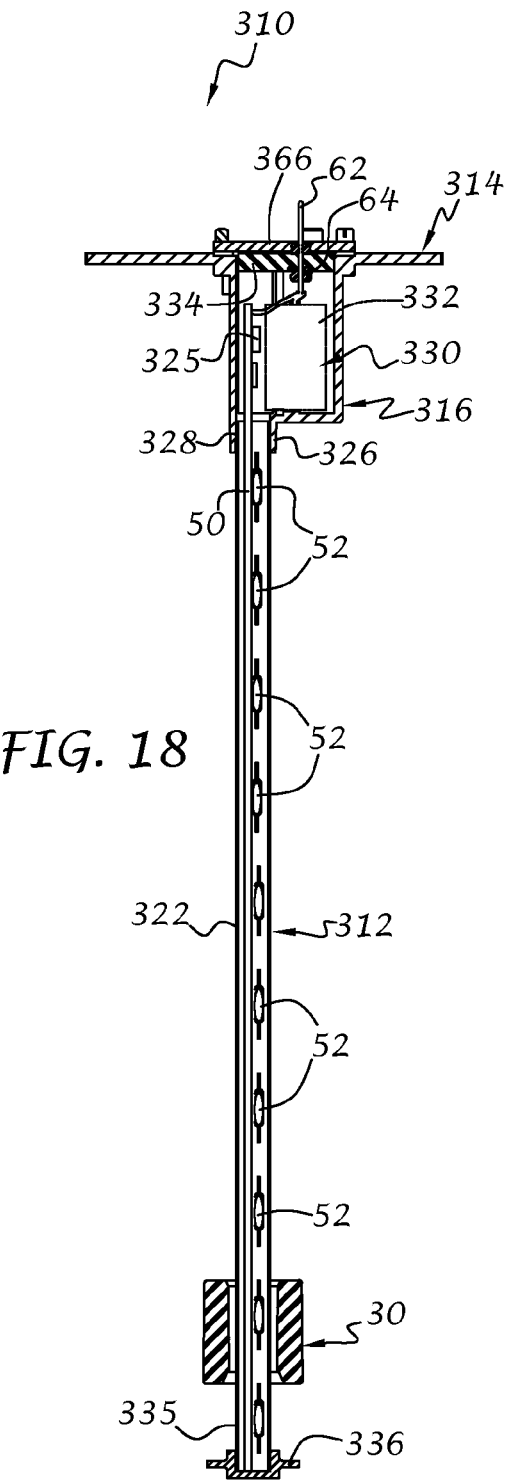

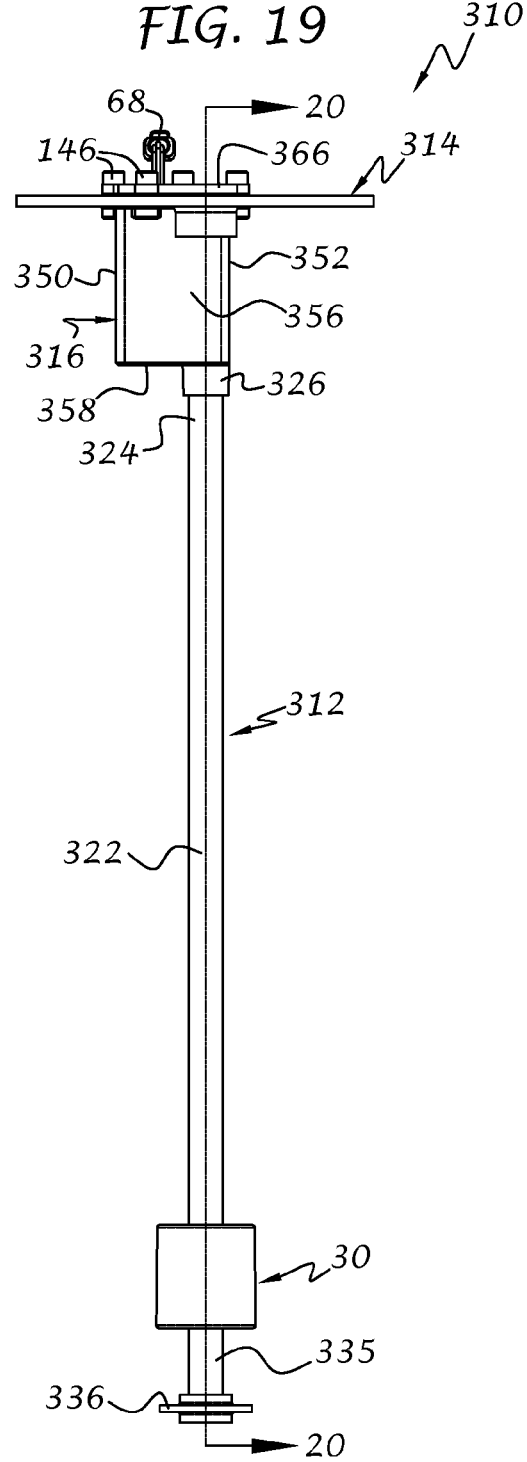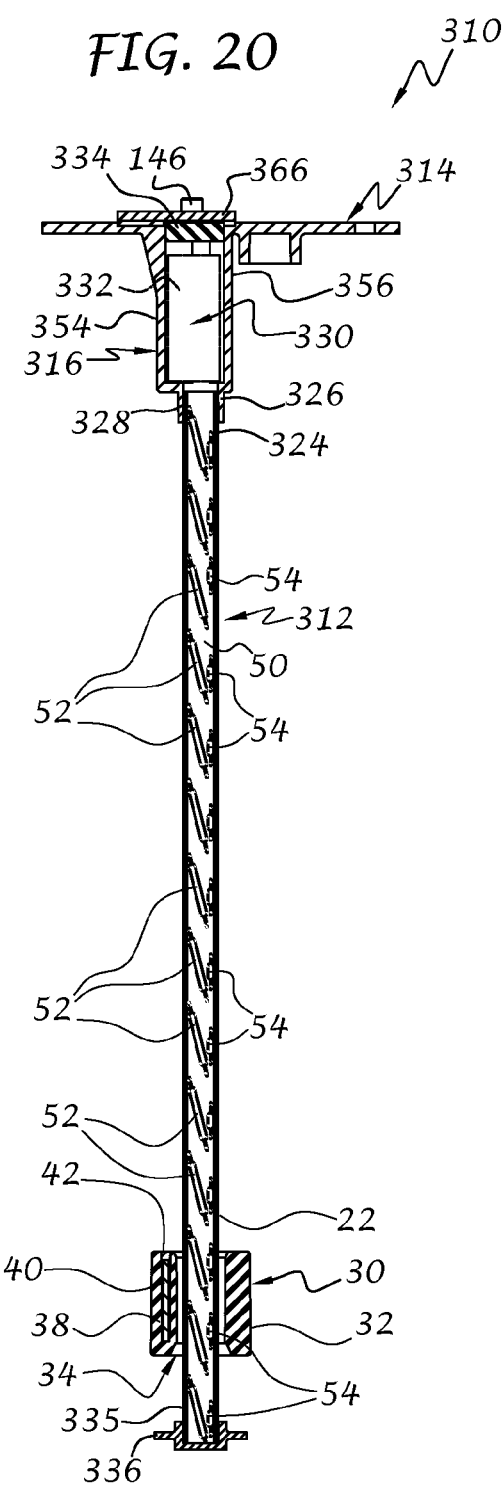

LIQUID LEVEL TRANSDUCER WITH INSERTABLE QUALITY SENSOR

BACKGROUND OF THE INVENTION

This invention relates to liquid level transducers and quality sensors, and more particularly to a liquid level transducer with a removable sensor module for determining the quality as well as other properties of the liquid being measured independent of liquid level determination.

Transducers for measuring liquid level are often used in vehicles, industrial equipment, as well as other mobile and stationary systems and components. The electrical output of such transducers varies in response to a change in the liquid level being measured and is typically in the form of a change in resistance, capacitance, current flow, magnetic field, and frequency. These types of transducers may include variable capacitors or resistors, optical components, Hall Effect sensors, strain gauges, ultrasonic devices, reed switch arrays, and so on.

In vehicles, industrial equipment and other systems powered by diesel fuel, a Selective Catalytic Reduction (SCR) system has been used to inject urea—a liquid-reductant agent—through a catalyst into the exhaust stream of a diesel engine. Urea sets off a chemical reaction that converts nitrogen oxides in the exhaust into nitrogen and water, which is then harmlessly expelled through the vehicle tailpipe. Previous urea quality sensor solutions have attempted to address industry quality control by ensuring that a specific quality of urea can be delivered into the exhaust gas stream. If the engine is operated without urea solution in the onboard urea tank, excessive NOx emissions can occur. Using a urea quality sensor, the SCR system can monitor the contents of the urea tank to alert an operator and/or system that the urea tank has been filled with other fluids, e.g., with tap water, coolant, windshield wiper fluid, oil, incorrect concentrations of urea solutions, and so on, instead of the correct concentration of urea solution. The introduction of a urea quality sensor into the SCR system also reduces the risk of tampering or accidental mis-filling and helps ensure compliance to environmental legislation, thus satisfying concerns of users and legislators alike. The urea quality sensor is intended to contribute to the overall success of SCR as a NOx reduction technology.

Besides monitoring the quality of DEF within the tank, the level of liquid in the tank must also be monitored to ensure that the DEF solution does not run out during operation. Accordingly, liquid level transducers have been used in conjunction with a quality sensor to determine both the level and the quality of the liquid within the tank. However, environmental regulations and/or the development and deployment of industry standards relating to diesel exhaust emissions have been largely unenforceable due at least in part to the lack of identifying a quality sensor that can meet the desired rigid standards. Consequently, many manufacturers of diesel-powered equipment provide DEF tanks with only a liquid level transducer, having opted to forego the added expense of providing quality detection solutions of the fluid within such tanks. When industry- or government-imposed standards are approved and enforcement of such standards becomes practical, DEF quality sensors may be required for both OEM and after-market applications. Under such conditions, prior art solutions do not provide built-in flexibility to retro-fit existing liquid level transducers with quality sensors. Accordingly, the manufacturer or end user may be faced with the expense of replacing a working liquid level transducer with a device that can detect both the liquid level and the quality of the fluid in the DEF tank, especially where the installation of in-line quality detectors may not be practical.

It would therefore be desirable to provide a liquid level transducer that can easily be upgraded to receive one or more interchangeable sensor modules for determining various properties of the fluid being measured. It would also be desirable to provide interchangeable modules that have different features or purposes dependent on or independent of the quality of liquid level within a tank.

SUMMARY OF THE INVENTION

In accordance with one aspect of the invention, an apparatus for determining at least first and second properties of a fluid associated with a tank includes: a mounting head adapted for connection to the tank; a housing extending from the mounting head; a chamber located within the housing adapted to receive the fluid associated with the tank; and a sensor module locatable in the chamber for determining the first property of the fluid. The sensor module is insertable and removable from the chamber without affecting determination of the second property of the fluid.

In accordance with a further aspect of the invention, an apparatus for determining at least first and second properties of fluid in a tank includes: a mounting head adapted for connection to the tank; a sensor probe extending from the mounting head for determining the first fluid property comprising a level of fluid in the tank; a housing extending from the mounting head; a chamber located within the housing adapted to receive the fluid associated with the tank; and a sensor module locatable in the chamber for determining the second property of the fluid. The sensor module is insertable and removable from the chamber without affecting determination of the level of fluid within the tank.

In accordance with another aspect of the invention, a method for using a liquid level transducer includes: providing a liquid level transducer with a mounting head for connection to a tank and a sensor extending therefrom for measuring a level of liquid within the tank; providing a chamber in the mounting head for fluid communication between the tank and a distal location to withdraw liquid from or return liquid to the tank; and providing a module for installation in the chamber for enhancing operation of the liquid level transducer. The module is operable to perform at least one function of a plurality of functions selected from the group comprising: measuring a quality of the liquid, measuring a composition of the liquid, measuring a pressure in the chamber, detecting the presence of vapor within the chamber, generating power for operating the transducer, determining a tilt or acceleration of the transducer, alerting unauthorized use or removal of the transducer, outputting a signal indicative of liquid level in accordance with predetermined parameters, performing RFID functions, and outputting a set of preselected signal parameters.

BRIEF DESCRIPTION OF THE DRAWINGS

The following detailed description of the preferred embodiments of the present invention will be best understood when considered in conjunction with the accompanying drawings, wherein like designations denote like elements throughout the drawings, and wherein:

FIG. 3 is a bottom right-rear isometric view thereof;

FIG. 4 is a top right-front isometric view thereof;

FIG. 17 is a left side elevational view thereof;

FIG. 18 is a sectional view thereof taken along line 18-18 of FIG. 17;

FIG. 19 is a rear elevational view thereof; and

FIG. 20 is a sectional view thereof taken along line 20-20 of FIG. 19.

Figure 1:
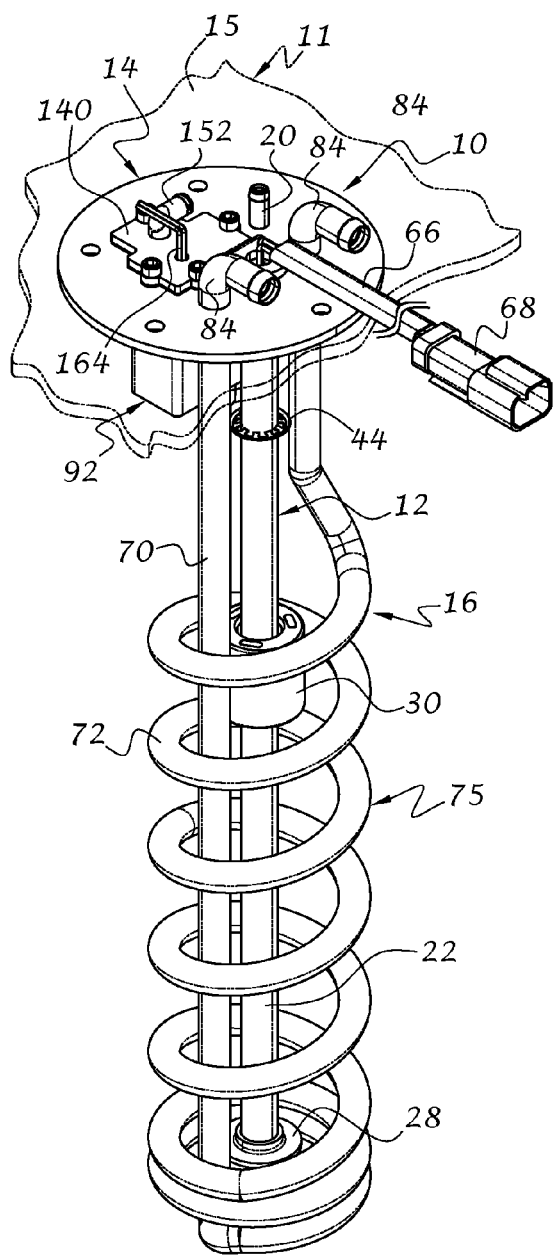
FIG. 1 is a top right-front isometric view of a liquid level transducer in accordance with an exemplary embodiment of the invention.
Figure 2:
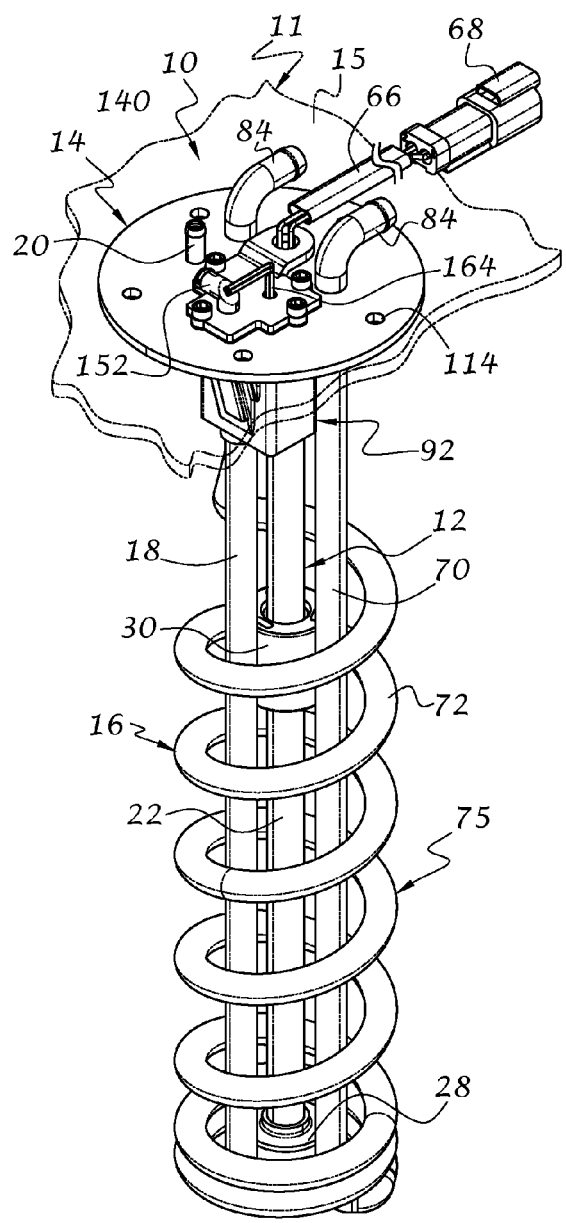
FIG. 2 is top right-rear isometric view thereof.

It is noted that the drawings are intended to depict only exemplary embodiments of the invention and therefore should not be considered as limiting the scope thereof. It is further noted that the drawings are not necessarily to scale. The invention will now be described in greater detail with reference to the accompanying drawings.

DETAILED DESCRIPTION OF THE INVENTION

Referring now to the drawings, and to FIGS. 1 through 5 in particular, a liquid level transducer or apparatus 10 in accordance with an exemplary embodiment of the present invention is illustrated. The liquid level transducer 10 preferably extends into a container or tank 11 (shown in phantom line in FIGS. 1 and 2), such as a fuel tank, oil reservoir, radiator, brake fluid chamber, or any other container for holding and/or transporting a liquid (not shown), as well as analyzing the quality and/or composition of the liquid within the tank.

The present invention is especially suitable for diesel-powered equipment, such as medium- to heavy-duty transportation trucks, light-duty passenger vehicles, farm and construction equipment, electrical generators, and so on, that utilize a selective catalytic reduction system (SCR) to reduce nitrogen oxide (NOx) emissions from the diesel-powered equipment where both the quantity of liquid within the tank and the quality and/or composition of the liquid is monitored. Such liquids can include diesel exhaust fluid (DEF) or AdBlue™ which ideally consists of a mixture of 32.5 percent pharmaceutical grade urea in deionized water. Although the invention will be largely discussed in context with a DEF holding tank, it will be understood that the present invention can be used with any tank or container where it is desirous to monitor the level of liquid within the tank as well as the quality and/or composition of the liquid stored, entering and/or leaving the tank. For example, the present invention can be used for both determining the level and quality and/or composition of different liquids contained within different tanks or containers associated with various equipment, such liquids including but not limited to, fuel, motor oil, transmission oil, antifreeze, brake fluid, water, various combinations of liquids, as additives, contaminants, and other constituents that may be associated with the liquids. Accordingly, it will be understood that the afore-mentioned vehicles, machines, emission reduction systems, as well as various liquids or combinations of liquids and constituents associated therewith, are given by way of example only, as the invention can be practiced with a wide variety of vehicles, machines, equipment, systems, and fluids without departing from the spirit and scope of the invention.

Although the transducer 10 is shown in the drawings with a vertical orientation, it will be understood that the transducer 10 can be configured for mounting in a horizontal orientation or any other suitable angle or orientation, without departing from the spirit and scope of the invention, such angle or orientation being dependent at least partially upon space constraints as dictated by the structure of the vehicle, machine, etc., with respect to the tank 11 and/or the particular shape and mounting requirements of the tank.

The transducer 10 preferably includes a mounting head 14 for connection to a wall 15 of the tank 11, an elongate probe assembly 12 extending downwardly from the mounting head 14, a heating unit 16 extending through the mounting head 14 and spiraling around the probe assembly 12, a fluid supply tube 18 extending through the mounting head 14 and along a substantial length of the heating unit 16 for delivering the contents of the tank 11 to a remote location, and a fluid return tube 20 extending through the mounting head 14 for returning unused contents to the tank.

Figures 5, 6:
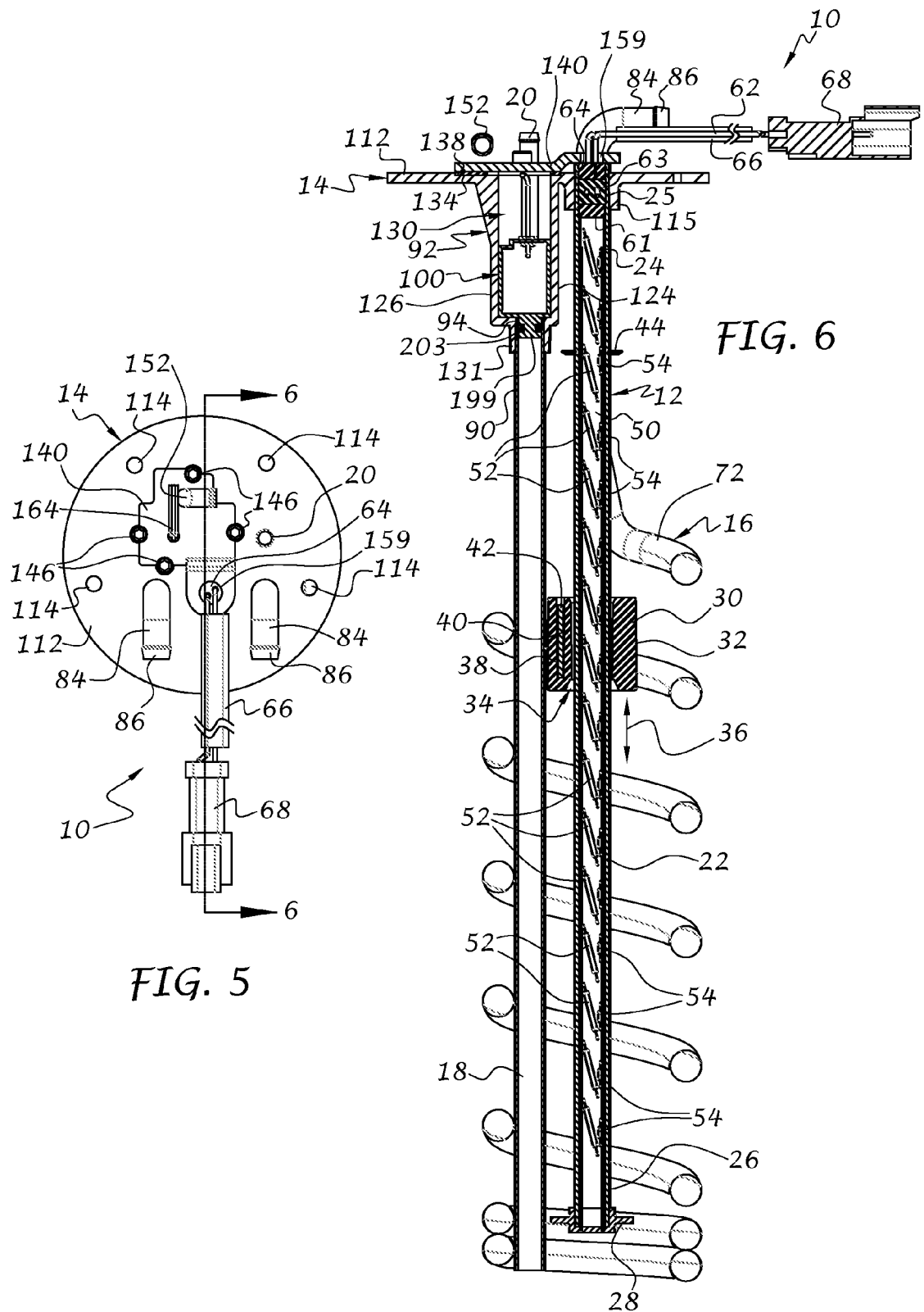
FIG. 5 is a top plan view of the liquid level transducer of the invention.
FIG. 6 is a sectional view thereof taken along line 6-6 of FIG. 5.
Figure 7:
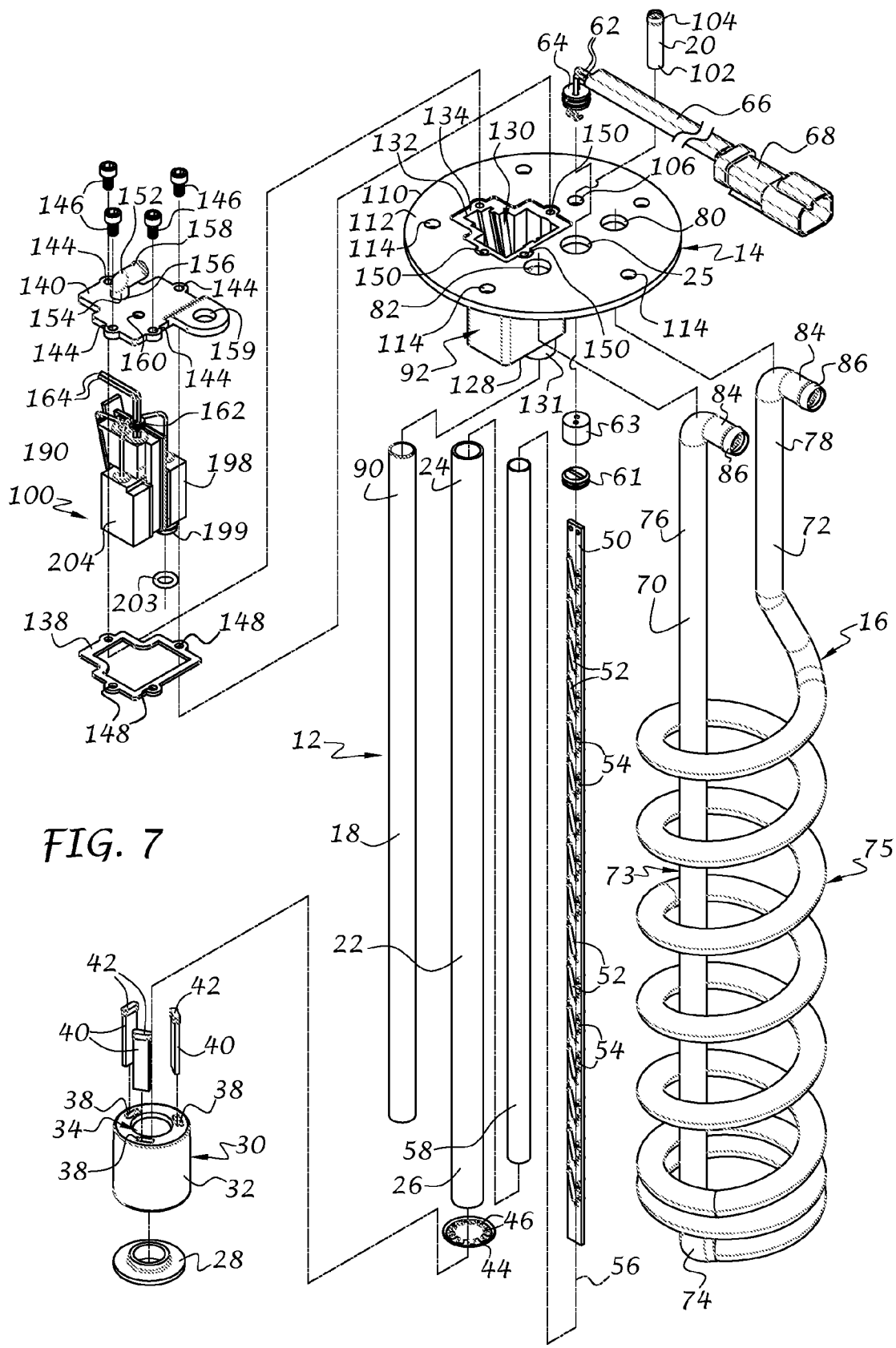
FIG. 7 is a top right-front exploded isometric view of the liquid level transducer of the invention.

As best shown in FIGS. 6 and 7, the probe assembly 12 is configured to sense liquid level in a linear direction and, in accordance with one preferred embodiment of the invention, includes an outer sensor tube 22 with an upper end 24 that is press-fit into a passageway 25 formed in the mounting head 14 and a lower end 26 that is press-fit into a lower support flange 28, which is generally annular in shape. It will be understood that the sensor tube 22 can be connected to the mounting head 14 and/or lower support flange 28 through other well-known connection means depending on the type of material used for the mounting head 14 and/or the sensor tube 22, such as surface welding (when both components are constructed of metal), adhesive bonding, mechanical fastening including threading or clamping, ultrasonic welding (when both components are constructed of plastic), and so on, without departing from the spirit and scope of the invention.

The probe assembly 12 further includes a float 30 having a cylindrically-shaped body 32 with a central bore 34 formed therein. The bore 34 is sized to receive the sensor tube 22 so that the float slides freely therealong, as represented by double arrow 36 in FIG. 6. The float 30 is preferably constructed of a closed-cell nitrile material, but may be constructed of other materials such as rubber, plastics, metal, and so on, without departing from the spirit and scope of the invention. It will be understood that the term "cylindrical" as well as its derivatives as may be used throughout the specification are given by way example only since the float 30, sensor tube 22, as well as structures or components of circular or annular cross-sectional shapes as shown throughout the drawing figures can be configured with other cross-sectional shapes such as square, triangular, octagonal or other multifaceted shapes, and so on. Thus, the invention is not limited to sensor tubes, floats, mounting heads, and other components of the liquid level transducer 10 that are shown as cylindrical, e.g. annular or circular in cross section, but can encompass any suitable cross sectional shape.

The float 30 preferably includes axially extending slots or openings 38 formed in the body 32 circumferentially about the central opening 34 for receiving one or more actuators 40 (FIGS. 6 and 7) and caps 42 for retaining the actuators 40 within the slots 38. Preferably, the holes are circumferentially spaced approximately 120 degrees apart. However, it will be understood that more or less holes, and thus actuators, can be located at different circumferential positions about the body 32 without departing from the spirit and scope of the invention. Preferably, each actuator 40 comprises a magnet having a generally flat or slightly curved elongate shape to accommodate the curvature of the float 30. Each magnet is preferably magnetized on its outer and inner faces such that magnetic flux lines of force are directed perpendicular with respect to the longitudinal extent of the magnet and toward the center of the opening 34 of the float 30. The magnets are preferably constructed of a hard ceramic ferrite material. However, it will be understood that the magnets can be constructed of other materials and may be of varying shapes without departing from the spirit and scope of the invention.

The sensor tube 22 is preferably constructed of a non-magnetic material such as plastic, aluminum, composites, and so on. The lower support flange 28 preferably serves as a lower stop for the float 30 in the event of a very low liquid level or empty condition of the tank. Likewise, an upper support flange or stop 44 is also annular in shape and, as shown in FIG. 6, surrounds the sensor tube 22 at the upper end 24 thereof to prevent further upward movement of the float 30 when the liquid level in the tank is at or above a predetermined level, such as at a full tank level. The upper stop 44 includes fingers 46 (FIG. 7) that extend generally radially inwardly and upwardly to contact the outer surface of the sensor tube 22, which permits sliding movement of the upper stop 44 in a downward direction as viewed in FIG. 7 during assembly so that the upper stop 44 can be adjusted to a desired height with respect to the sensor tube 22. The slightly upward extension of the fingers 46 prevent sliding movement of the upper stop 44 in the upward direction to thereby lock the upper stop 44 against upward movement when the float contacts the upper stop at a full tank condition.

As best shown in FIGS. 6 and 7, a sensor board 50, preferably in the form of a printed circuit board (PCB), is located in the sensor tube 22 and extends along a substantial length thereof. One or more electronic sensors 52 are located on the PCB and are responsive to one or more of the actuators 40 for indicating a change in liquid level as at least one of sensors changes states. Preferably, the sensors 52 comprise a plurality of normally-open reed switches positioned along the length of the PCB 50 in series with a plurality of resistors 54. The reed switches are shown oriented at an acute angle with respect to a longitudinal axis 56 (FIG. 7) of the sensor tube 22 (and thus the PCB 50) and are responsive to the magnet(s) 40 in the float 30 for creating a liquid level signal, in conjunction with the resistors 54, as the float rides along the sensor tube 18 in response to a change in liquid level within the tank.

Insulating material, such as an inner tube 58, which can comprise heat-shrink tubing and/or potting material, and the like, can be located between the PCB 50 and the sensor tube 22 to insulate and protect the reed switches 52 and other components against shock, vibration, and other harsh conditions to which the transducer 10 may be exposed. Although a particular number of reed switches, spacing between reed switches and the angle of the reed switches are shown, it will be understood that the particular number of reed switches as well as their corresponding resistors and other electrical components, their spacing, orientation, and placement on one or both sides of the PCB can greatly vary without departing from the spirit and scope of the invention.

The arrangement of three magnets at 120 degrees apart around the circumference of the float 30 advantageously concentrates a large magnetic field at the center of the float opening 34, and thus effectively saturates one or more of the reed switches 52 that may be present within the opening 34 (depending on the number, size, and spacing of the reed switches on the PCB) to thereby create a positive latching or closing effect. Once the float has moved above or below the reed switch, the reed switch will more effectively return to its normally open state due to the relatively low residual magnetic field at the upper and lower ends of the magnets. Thus, by magnetizing the relatively broad inner and outer faces of each magnet, and orienting them so that their flux lines are directed to the axial center of the float, the switching effect of the reed switches can be more closely controlled, thereby creating more reliable activation and deactivation of the reed switches. In this manner, the prior art disadvantages associated with inaccurate liquid level measurement due to false switching are substantially reduced. It will be understood that more or less magnets can be located around the circumference of the float without departing from the spirit and scope of the invention.

Still referring to FIGS. 6 and 7, electrical wires 60 and 62 preferably extend from the sensor board 50, through a PCB support 61 that centers the PCB in the tube 22, an insulating grommet 63 positioned in the tube 22, and a strain relief grommet 64 located in the passageway 25 of the mounting head 14, through a protective sleeve 66, and terminate at an electrical connector or plug 68 for receiving a complementary connector or plug (not shown) associated with further processing and/or display circuitry (not shown) of the vehicle, machine, system and so on, with which the liquid level transducer 10 is associated. The support 61 and grommets 61, 64 can be constructed of an elastomeric material or the like to thereby seal around the wires 60 and 62 and seal against the inner wall of the passageway 25 of the mounting head 14.

It will be understood that the sensors 52 can comprise normally closed reed switches. However, it will be understood that other magnetic sensing devices can be used without departing from the spirit and scope of the invention. For example, other devices can include, but are not limited to, one or more solid state magnetic flux field sensors connected to the sensor board 50, Hall effect sensors, magnetoresistive (MR) sensors, anisotropic MR (AMR) sensors, giant magnetoresistance (GMR) sensors, solid state Micro-Electro-Mechanical Systems (MEMS), magnetic switches. With the use of magnetic flux field or Hall effect sensors, a single sensor may be sufficient to determine the position of the magnet and thus the level of liquid within the tank depending on its length. Where the measurement length is too long for a single flux field sensor, a sufficient number of sensors placed at predetermined positions along the sensor board or on the surface of the sensor tube 22 itself can be used. In addition, when using a sensor that changes state in the presence and/or absence of a magnetic field, the magnets need not be arranged circumferentially as shown, nor is it an absolute requirement that three magnets be used, since one or more magnets may be adequate depending on the sensing technology used. Thus, the present invention is adaptable to a wide variety of liquid level sensing technologies.

Moreover, other types of sensors that change in an electronically measurable manner in response to the proximity, presence, and/or absence of one or more actuators can be used, including for example nonmagnetic sensing technologies such as proximity detectors using capacitance, optical, or other measurement technologies, and so on. Likewise, the actuator can be in the form of one or more LED's, optical fibers or other light sources, or other contactless actuator/sensor arrangements to remotely change the electrical state of one or more sensor elements. In the event that optical sensors are used, the sensor tube 22 can be formed of a material that is translucent or transparent to the wavelength of the light source so that the sensor elements can readily detect movement of the light source in response to float movement as the liquid level in the container rises and falls.

Furthermore, other liquid level measurement technologies can be used for such as resistance cards and wiper arms, resistance wires or thick film devices that utilize the fluid as a heat sink to determine liquid level, capacitance or impedance measurement technologies where the liquid being measured functions as a dielectric or insulator, current flow, frequency, tuning forks, strain gauges, ultrasonic or other time domain devices, and so on.

The sensor tube 22 can also contain other sensors besides liquid level, in particular temperature, which would provide information to a heating circuit for controlling circulation of heating fluid through the heating unit 16 when the contents of the tank are subjected to slushing or solidifying at lower operating temperatures. Wiring connections and any circuitry required for sensors and sensing operations can be located within the sensor tube.

The heating unit 16 is preferably in the form of a single, elongate tube with a first leg 70, a second leg 72, and a bend 74 extending between the first and second legs. As shown, the first leg 70 includes a relatively straight section 73 and the second includes a coiled section 75 that spirals around the straight section 73. The first and second legs 70 and 72 also include straight upper segments 76 and 78, respectively, that extend through respective openings 80 and 82 formed in the mounting head 14. The upper segments 76 and 78 are preferably sealed to the openings 80 and 82, respectively, through surface welding, press-fitting, adhesive bonding, or other known connecting means so that the contents of the tank 11 (FIG. 1) are isolated from the environment outside of the tank. The outer distal ends 84 of the upper segments 76, 78 are bent at approximately 90 degrees and include a barb 86 for connection to supply and return conduits (not shown) of a fluent heat source, such as such as engine coolant, oil, hot exhaust gases and so on, in order to provide constant and/or intermittent circulation of heating fluid into the tank 11 to warm the contents of the tank. When the coil carries warm fluid, such as engine coolant, the heat transferring from the coil is used to thaw or prevent freezing of the tank contents surrounding the sensor elongate probe assembly 12, including the sensor tube 22 and its sensing elements as previously described, the float 30, and the fluid supply tube 18. The coiled section 75 of the heating unit 16 increases the amount of available surface area of the heater tubing and thus the amount of heat transfer available to warm the contents of the tank.

A substantial portion of the fluid supply tube 18 is preferably located within the coiled section 75 of the heating unit 16 so that any frozen content within the supply tube can be quickly thawed when the vehicle or equipment associated therewith is started. The fluid supply tube 18 preferably includes an upper segment 90 that is coincident with a passageway 94 formed in an integral housing 92 of the mounting head 14 and is connected and sealed thereto through well-known connecting means, as described above with respect to the heating unit 16.

The housing 92 is adapted to receive one or more interchangeable modules 100 (FIG. 7) or modules 100A and/or 100B (FIG. 8) having different features related to sensing, detecting, transmitting signals, filtering, and so on, as well as combinations thereof. In accordance with an exemplary embodiment of the invention, the module 100 comprises a sensor module for determining the properties of the liquid within the tank, which may include determining the liquid quality, composition, age of the liquid, the presence of contaminants and/or foreign material, as well as other properties of the tank contents. Exemplary features of the sensor module 100 will be described in greater detail below.

The return tube 20 includes a lower section 102 that extends through an opening 106 (FIG. 7) of the mounting head 14 and an upper barbed section 104 for connection to a return conduit (not shown) associated with the vehicle or equipment to which the tank 11 (FIG. 1) is connected. The lower section 102 is preferably sealed to the opening 106 through known connecting means, as described above with respect to the heating unit 16, so that the contents of the tank 11 (FIG. 1) are isolated from the environment outside of the tank.

The supply tube 18 and return tube 20 are adapted for connection to a pump or the like in a well-known manner for delivering liquid from the tank to a remote location and returning unused liquid back into the tank. If desired, a filter (not shown) can be located at the upper end and/or the lower end of the supply tube 18 inside the tank. In accordance with a further embodiment of the invention, the liquid supply tube 18 and return tube 20 can be reversed, in that the return tube can be connected to the housing 92 for monitoring various properties of the liquid returning to the tank.

Referring now to FIGS. 6-12, the mounting head 14 preferably includes a body 110 with a circular plate-shaped mounting flange 112 having the passageway 25 (FIG. 7) and openings 80, 82, and 106 formed therein. A collar 115 is integrally formed with the body 110 and extends downwardly therefrom. The collar is coincident with the passageway 25 for receiving the sensor tube 22. Mounting apertures 114 extend axially through the mounting flange 112 for mounting the transducer 10 to the wall 15 (FIG. 1) of the tank 11 or the like. The mounting apertures are adapted to receive threaded studs (not shown) connected to the tank wall 15 and extending outwardly therefrom in a well-known manner, so that during installation, the mounting apertures 114 are in alignment with the studs protruding from the tank wall. The transducer 10 is then pushed toward the tank wall 15 with the studs extending through corresponding mounting apertures 94. Nuts (not shown) or other internally threaded components are then secured on the studs and torqued until the transducer 10 is secured on the wall 15.

It will be understood that the tank-mounted studs can be replaced with screws or bolts or the like, that extend through the mounting apertures and thread into threaded apertures (not shown) in the tank wall 15. Other means for mounting the transducer 10 to the tank 11 can be used without departing from the spirit and scope of the invention.

Moreover, it will be understood that the mounting head 14 is not limited to a flange mounting arrangement as shown, as other means for mounting the liquid level transducer 10 to a tank or other container can be used, including NPT type threads, clamping, welding, and so on, without departing from the spirit and scope of the invention. It will be further understood that the mounting head can be constructed of metal, such as brass, aluminum, stainless steel, and so on, or other materials such as plastic or ceramic.

As best shown in FIGS. 3 and 4, the housing 92 includes spaced upright side walls 120 and 122, spaced upright front and rear walls 124 and 126 extending between the side walls, and a bottom wall 128 extending between the upright walls. The upright walls 120, 122, 124, and 126 are preferably integrally formed with the body 110 and extend downwardly therefrom to define a hollow interior space or chamber 130 (FIGS. 6-9, 11, and 12). A collar 131 is integrally formed with the bottom wall 128 of the housing 92 and extends downwardly therefrom. The collar 131 is coincident with the passageway 94 for receiving the fluid withdrawal tube 18 so that the chamber 130 is in fluid communication with the contents of the tank 11 (FIG. 1).

Figure 8:
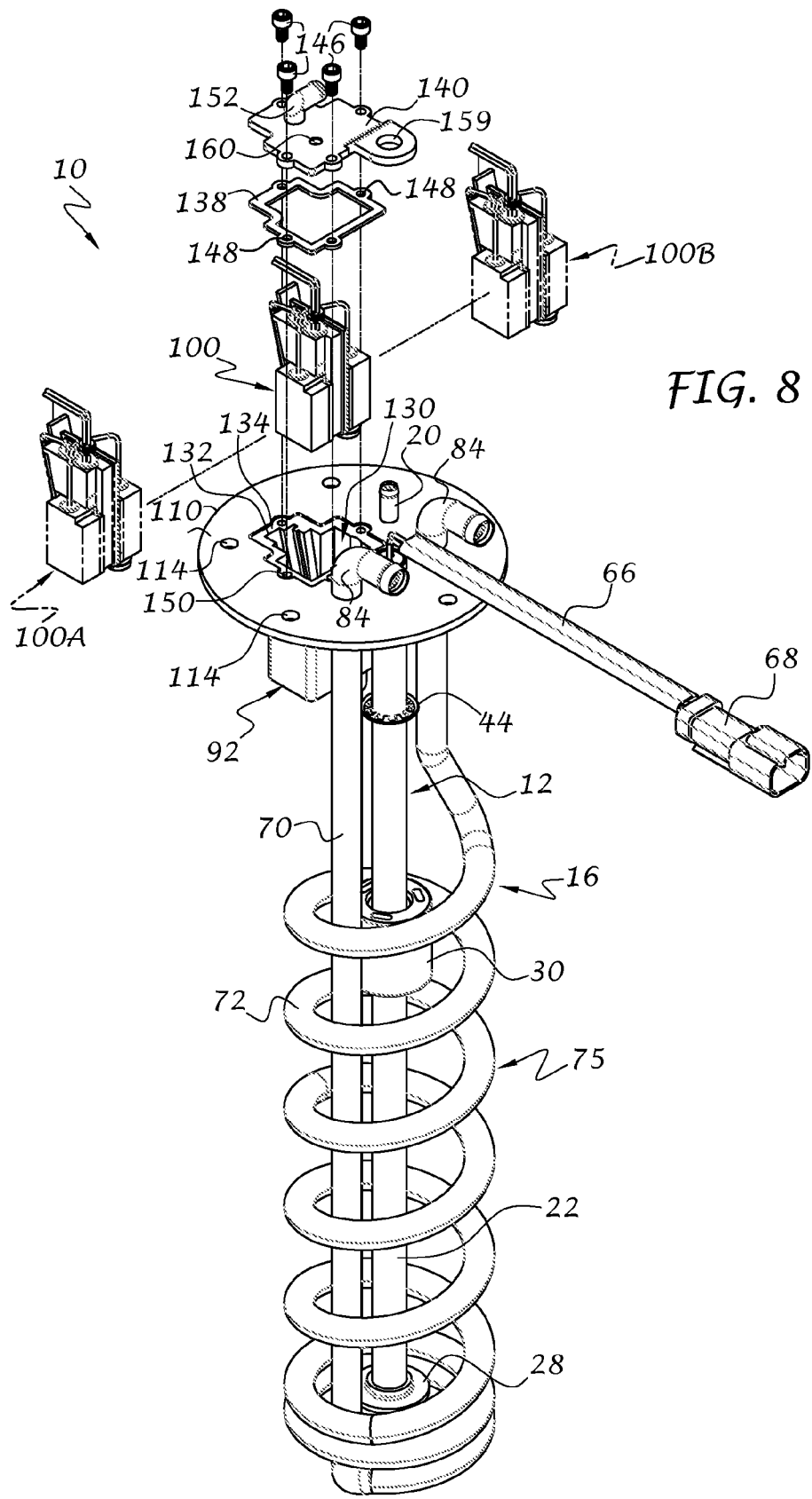
FIG. 8 is a top right-front partially exploded isometric view thereof showing a fluid quality and/or composition sensor module as well as other modules with different functions that can be installed and removed from a mounting head of the liquid level transducer in accordance with an exemplary embodiment of the invention.

Referring to FIGS. 7 and 8, an access opening 132 is formed in the body 110 coincident with the housing 92. A depression 134 is formed around the periphery of the opening 132 for receiving a seal or gasket 138. A top plate or cover 140 is removably connected to the mounting head 14 and fits over the access opening 132 to enclose the chamber 130 and its contents. To that end, the cover 140 can include a body or plate 142 with an outer periphery similar to the outer periphery of the access opening 132. Mounting apertures 144 are formed in the body 142 for receiving fasteners 146 that also extend through apertures 148 in the gasket and thread into apertures 150 in the mounting head 14 to removably connect the cover 140 to the mounting head 14 with the gasket 138 sandwiched therebetween to thereby seal the chamber 130 from the outside environment.

A supply tube fitting 152 preferably includes a lower section 154 that is coincident with and extends into an opening 156 formed in the an integral chamber or housing 92 of the cover 140, and an upper barbed section 158 for connection to a supply conduit (not shown) associated with the vehicle or equipment to which the tank 11 (FIG. 1) is connected. The lower section 154 is preferably sealed to the opening 156 through known connecting means, as described above with respect to the heating unit 16, so that the contents of the tank 11 (FIG. 1) and the housing 92 are isolated from the environment outside of the tank. It will be understood that the supply tube fitting 152 can be integrally formed with the cover 140 during manufacture through well-known forming means such as machining, casting, injection molding, and so on, depending on the material(s) selected for the cover 140 and the fitting 152.

A first opening 159 (FIG. 7) is formed in the cover 140 for receiving the wire grommet 64 associated with the elongate probe assembly 12 for measuring liquid level. Likewise, a second opening 160 (FIG. 7) is formed in the cover 140 for receiving a wire grommet 162 associated with wires 164 of the sensor module 100 for connecting to further electronics, such as but not limited to, a processor, display, transmitter, and so on, associated with the vehicle or equipment for relaying information about the fluid being measured to a user and/or control system for controlling or metering distribution of the liquid within the tank, monitoring the quality and/or composition of the liquid, alerting an operator or down line system when the tank has been filled with incorrect liquid for preventing damage to expensive components such as a catalytic converter when the tank holds a quantity of DEF fluid or the like, to control operation of the vehicle or equipment in the event that the liquid does not meet minimal quality and/or composition standards or requirements, and so on. In the event that the sensor module 100 comprises one or more filters for removing contaminants from the liquid as it exits the tank, the information can also include filter efficiency, differential pressure across the filter for determining when it should be replaced, unauthorized tampering or theft of the module 100 or transducer 10, detection of antifreeze or other coolant that may leak into the tank from the heating unit 16, fluid flow through the module for metering the quantity of fluid that may be transferred to another portion of the vehicle or machine, pressure and/or temperature of the fluid within the module, and so on, for additional display and/or processing with one or more control systems associated with the vehicle or machine. Such information can be sent to the control system via hardwire connection or wireless transmission of data from the transducer 10. Accordingly, it is contemplated that the module 100 can include any apparatus, assembly, sensor, or device for measuring and/or controlling fluid properties or parameters that can be installed and removed separately and independently from the function of the liquid level sensing portion of the transducer 10.

Figure 11:
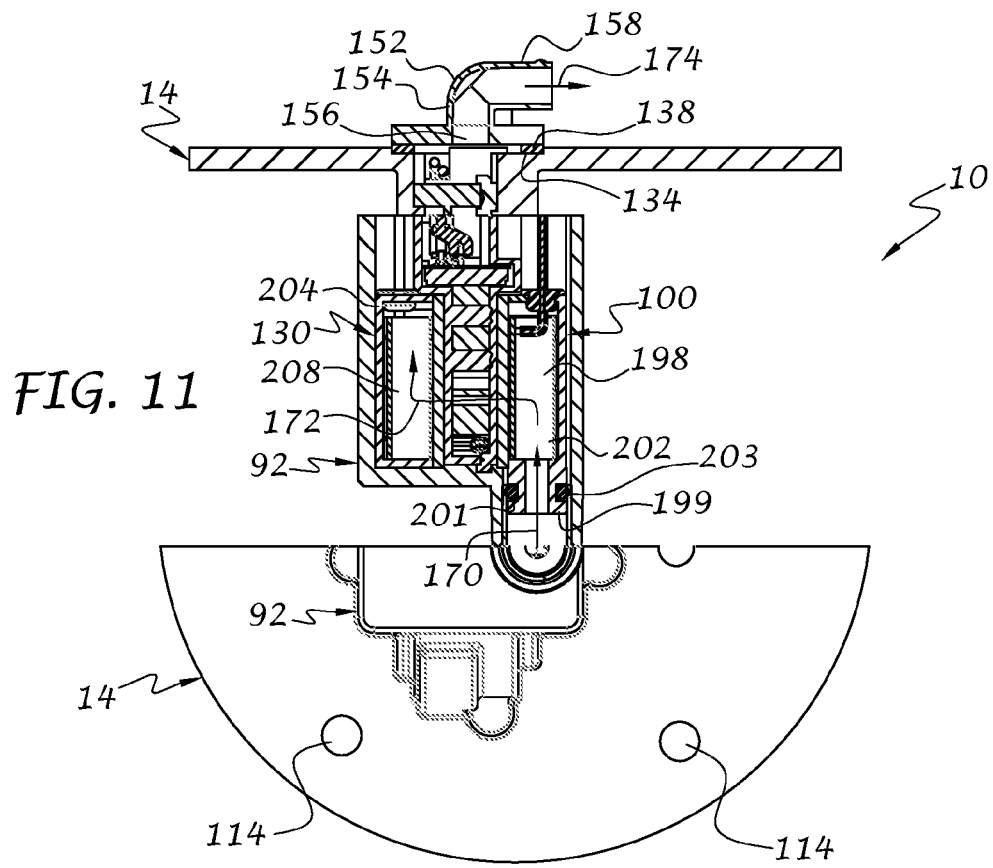
FIG. 11 is a sectional view of the liquid level transducer taken along line 11-11 of FIG. 10 showing the fluid quality sensor module installed.

As shown in FIGS. 8, 9, 11, and 12, the sensor module 100 is removably connected to the mounting head 14 of the transducer 10. The module 100 preferably operates independently of the liquid level measurement system previously described, such that the presence or absence of the module 100 does not affect liquid level measurement. Likewise, the absence of the liquid level measurement system does not affect the function (s) associated with the module 100. In FIG. 8 for example, the module 100 is shown as being installed in or removed from the chamber 130 of the housing 92 of the mounting head 14. Likewise, FIG. 11 shows the module 11 installed in the chamber 130 with fluid flow from the tank into the entrance of the chamber 130 represented by arrow 170, fluid flow through the module 100 represented by arrow 172, and fluid flow exiting the chamber 130 through the supply tube fitting 152 represented by arrow 174 for transferring the fluid from the module 100 to a downstream location.

Figure 9:
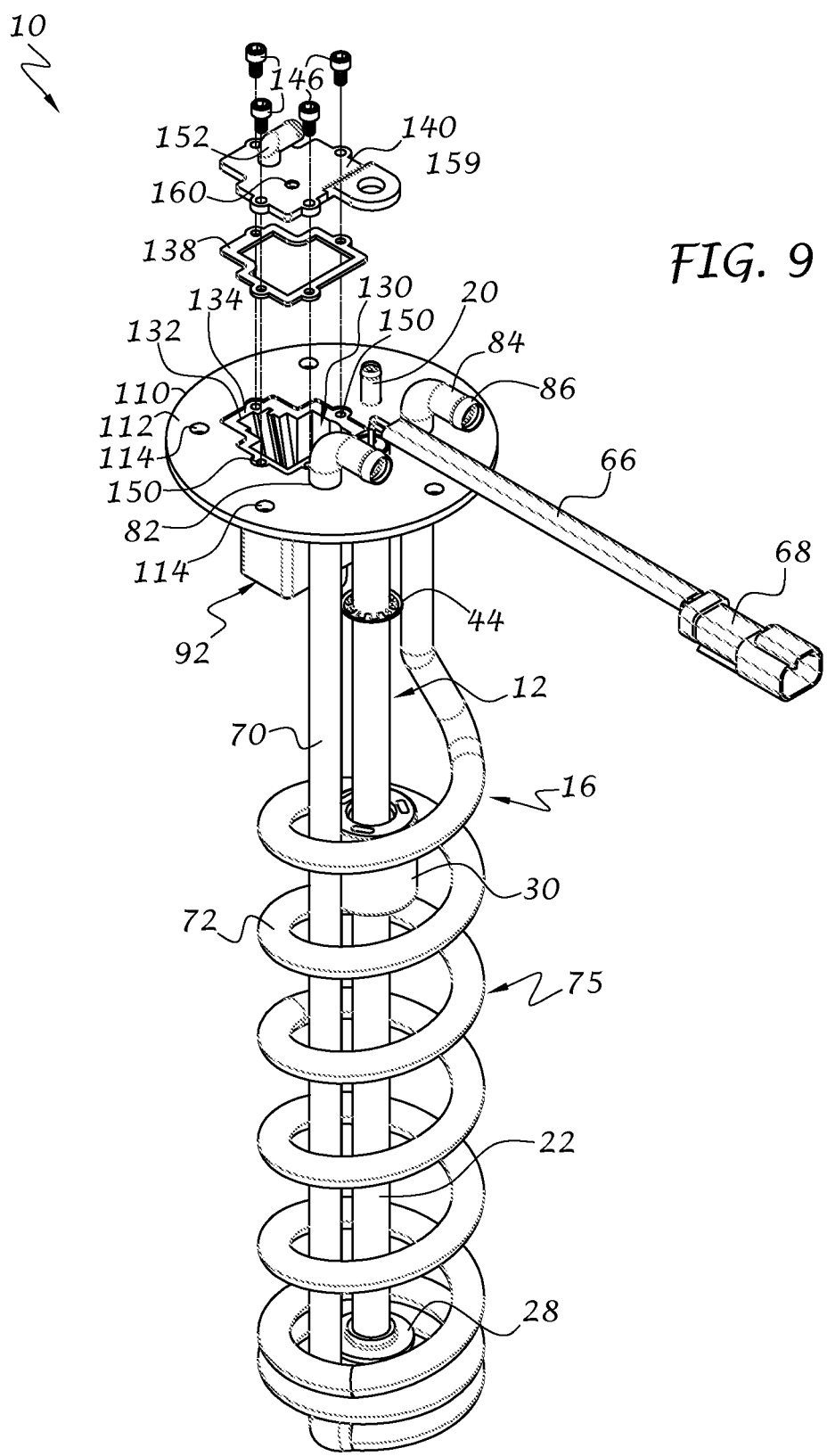
FIG. 9 is a view similar to FIG. 8 with the fluid quality sensor module removed in accordance with the invention.
Figure 10:
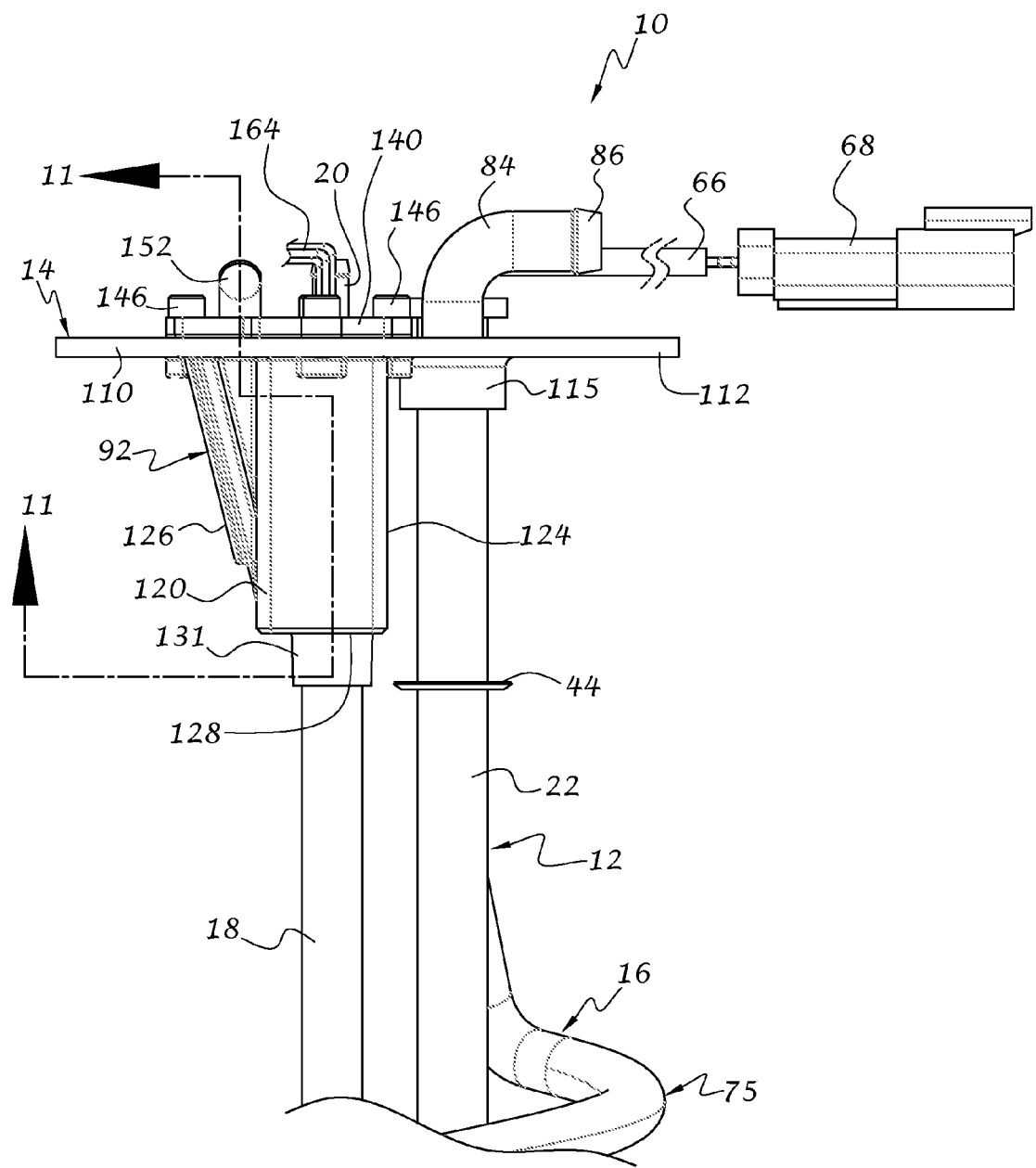
FIG. 10 is an enlarged right side view of an upper portion of the liquid level transducer.
Figure 12:
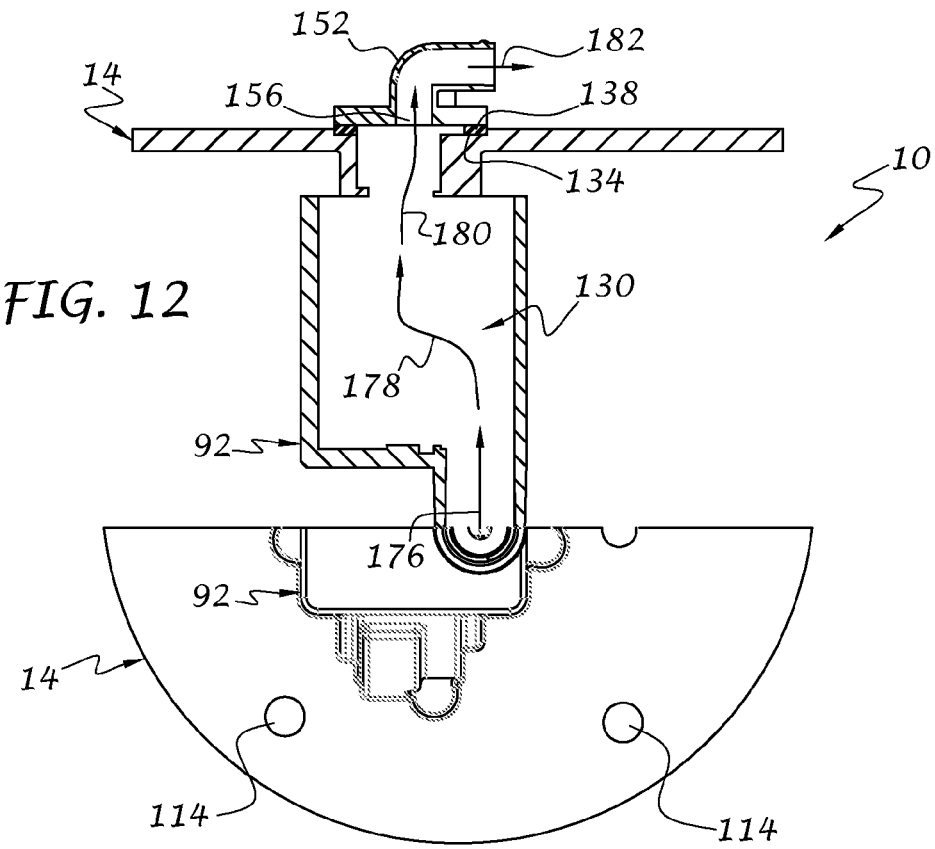
FIG. 12 is a sectional view similar to FIG. 11 with the fluid quality sensor module removed.

Moreover, in FIG. 9 for example, the module 100 is shown as being absent from the chamber 130 of the housing 92 of the mounting head 14. Likewise, FIG. 12 shows the chamber 130 of the housing 92 absent the module 100, with fluid flow from the tank into the entrance of the chamber 130 represented by arrow 176, fluid flow through the chamber 130 represented by arrows 178 and 180, fluid flow exiting the chamber 130 through the supply tube fitting 152 represented by arrow 182 for transferring the fluid from the tank to a downstream location. It will be understood that when the module 100 is removed, the cover 140 can be replace with another cover (not shown) to completely seal the chamber from the transfer of fluid when the supply of fluid to a downstream location is not needed. Accordingly, the transducer 10 can be used without the module 100 until such time that it is determined that the module 100 is needed, thus creating a module-ready transducer 10.

Figure 13:
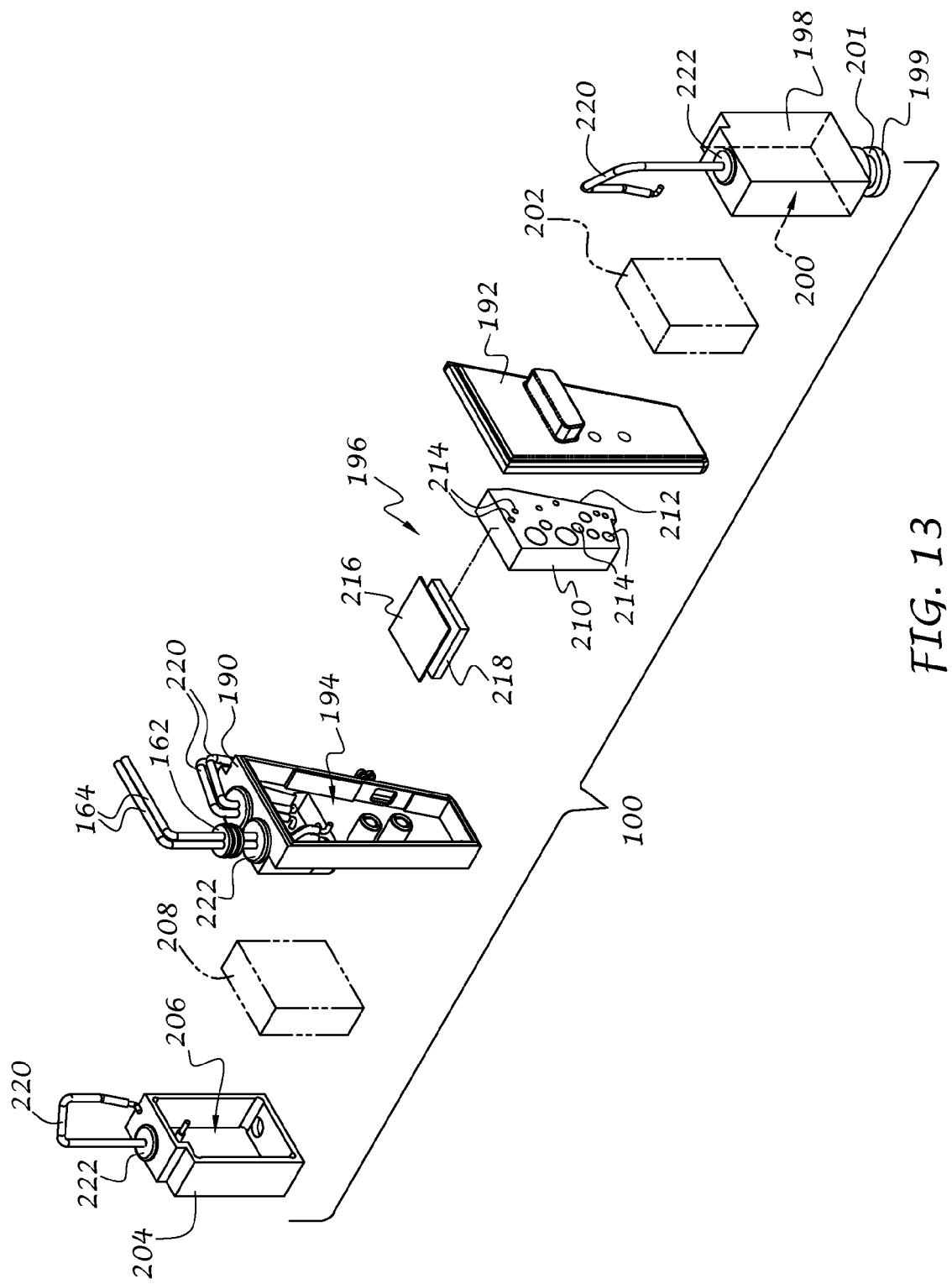
FIG. 13 is a top left-front exploded isometric view of an exemplary fluid quality sensor module.

Referring now to FIG. 13, the sensor module 100 in accordance with an exemplary embodiment of the invention includes a first housing section 190 with a first cover 192 connected thereto to form a first hollow space or compartment 194 within which a first device 196 is positioned. The first device preferably comprises an optical sensor assembly 196 for determining the quality of a liquid passing through the chamber 130 (FIGS. 7, 11) and/or content and other properties of the liquid being measured. A second housing section 198 is connectable to one side of the cover 192 of the first housing section 190 to form a second hollow space or compartment 200 (represented by hidden line) within which a second device 202 (shown in phantom line) can be located. Likewise, a third housing section 204 is connectable to an opposite side of the first housing section 190 to form a third hollow space 206 within which a third device 208 (shown in phantom line) can be located. As shown in FIGS. 7, 11, and 13, the second housing section 198 includes a tubular projection 199 that extends downwardly into the withdrawal tube 18. An annular groove 201 is formed in the tubular projection 199 for receiving an O-ring 203 to thereby seal the second housing section 198 and the withdrawal tube 18 together. This sealing arrangement facilitates quick installation and removal of the module 100 with respect to the chamber 130.

The optical sensor assembly 196 includes a prism 210 with a sensing surface 212 and light blocking apertures 214 to direct radiant energy from a light source (not shown) associated with circuitry 216 toward the sensing surface 212, reflect or refract radiant energy from the surface 212 in the presence or absence of liquid, and direct the reflected and/or refracted radiant energy to an optical sensor 218. A suitable optical sensor can includes an optical chip or the like having a two-dimensional array of sensors or pixels for determining the presence, intensity, color, and position of radiant energy reflected and/or refracted from the sensing surface 212.

Signals from the optical sensor 218 can then be analyzed by the circuitry 216, which can include a printed circuit board (PCB) with a microprocessor and other supporting electronic components operably connected thereto, to determine the quality, composition, as well as other properties of the liquid as it comes in contact with the sensing surface 212 in the chamber 130 (FIG. 7). Depending on the refractive index of the liquid being measured, the refracted and/or reflected light reaching the optical sensor 218 changes. The difference in the position of radiant energy on the optical sensor 218, as well as the intensity, color, the presence or absence of radiant energy at certain locations of the optical sensor 218, as well as other factors, can be monitored to determine properties of liquids to a high degree of accuracy. Further details of the optical sensor assembly 196 can be found in U.S. Pat. No. 8,934,102 to Wirthlin, et al. issued on Jan. 13, 2015, the disclosure of which is hereby incorporated by reference.

The second device 202 and third device 208 located in their respective compartments 200 and 206, can function independently or together to determine for example the impedance of liquid located in or passing through the chamber 130 (FIGS. 7 and 11). Electrical conductors or wires 220 (FIG. 13) are connected to the PCB 216 and extend through a first grommet 222 associated with the housing sections 198, 204. Likewise, electrical conductors or wires 164 are connected to the PCB 216 and extend through the grommet 162 associated with the cover 140 (FIG. 7) so that power can be provided to the circuitry and signals from the circuitry, which are linked to one or more of the devices 196, 202 and 208, can be sent to the vehicle system for further processing and/or display.

When one or both devices 202 and/or 208 are configured for impedance measurements, which may include determining capacitive, resistance, and/or inductance of the liquid being measured for example, further properties of the liquid can be measured that the optical sensor assembly may not be able to recognize due to different materials exhibiting similar refractive indices or the like. Accordingly, the combination of impedance and optic measurements of the liquid provide the user and/or system associated with the vehicle or equipment with more information regarding quality and/or composition of the liquid. With the dual system of measurement, manual or automated decisions that impact further operation of the system can be decided with a greater degree of certainty.

For example, Selective Catalytic Reduction (SCR) systems where a certain percentage of urea is mixed with deionized water to form DEF, is injected through a catalyst into the exhaust stream of a diesel engine. Urea sets off a chemical reaction that converts nitrogen oxides in the exhaust into nitrogen and water, which is then harmlessly expelled through the vehicle tailpipe. If the engine is operated without urea solution in the onboard urea tank, excessive NOx emissions can occur. Using a urea quality sensor that can quantify the percent urea within the deionized water, determining whether or not the liquid within the tank comprises other fluids, e.g., urea with tap water, farm-grade urea with tap water, coolant, windshield wiper fluid, oil, incorrect concentrations of urea solutions, and so on, the operator and/or system can determine with greater accuracy how the vehicle or equipment should operate in order to reduce excessive emissions and avoid damaging expensive components such as the catalytic converter.

Accordingly, by having more information available to the user and/or system, it can be determined for instance if the engine should not be operated or operated at a reduced power output until the tank is filled with proper solution. Moreover, when the percent urea to deionized water or other solution used to accomplish reduction in NOx emissions outside of established standards, the sensor module 100 of the invention is capable of providing information to vary how much liquid is metered to the exhaust system in a closed loop configuration that includes the NOx sensor of the vehicle or equipment.

With the above features of the invention in mind, the second and third devices can operate together where the first device includes a first electrode and the second device includes a second electrode with the liquid being measured located therebetween for determining electrical properties of the liquid, and thus identify the liquid quality and/or composition, as previously discussed.

Moreover, in accordance with a further embodiment of the invention, the second and third devices can operate independently. For example, the second device can include a filter for removing contaminants from the liquid before reaching the optical sensor assembly and the third device. The third device in this instance may be an impedance sensor having a pair of spaced electrodes with fluid therebetween for measuring the properties of the fluid, so that the first, second, and third devices operate independently. Accordingly, the mounting head of the present invention is configured with an integral chamber that allows various functional devices to be removably embedded.

It will be understood that the first, second and third devices are not limited to the particular examples given, but may include any technology that determines fluid quality and/or composition, any device or apparatus that modifies the fluid including, but not limited to, one or more filters for removing contaminants from the fluid, pumps, mixing chambers, metering valves or flow regulators, and so on, and any apparatus that would be useful for processing liquid level signals, such as one or more tilt sensors or acceleration sensors, vapor sensors, pressure sensors, as well as transmitters, receivers, transceivers, power generating devices, and so on. Such devices can be readily replaced or exchanged for other devices of similar or different functions to thereby provide a liquid level transducer that is adaptable to a wide variety of functions depending on the particular needs of the vehicle or equipment with which the transducer 10 is associated. Where the particular module does not need to interact with fluid to accomplish its operation(s), the module can include a plug or fluid blocking member to seal the passageway 94 (FIG. 6) and prevent the ingress of fluid into the chamber from the tank.

It will be understood that the sensor module of the invention is not limited to three devices, but more or less devices or mechanisms can be provided without departing from the spirit and scope of the invention.

Although a particular shape of the mounting head, including the integral chamber, is shown, it will be understood that the mounting head is not limited to a single chamber or chambers having a particular shape. For example, one or more chambers integral to the mounting head 14 can be circular with a circular cover or plate or of any other suitable shape that can be installed and removed for replacing one or more modules and/or one or more devices associated with the modules, The cover or plate can be configured for installation and removal for example by twisting, snap-fit engagement of the components, bolting, clamping including over-center clamp mechanisms, and so on.

In accordance with a further aspect of the invention, and with reference to FIG. 8, different modules, such as 100A and 100B shown in phantom line for example, can be associated with different operations or functions, such as optical and/or electrical fluid analysis, fluid filtering, fluid pumping, and so on, can be provided in interchangeable or kit form for modifying the transducer 10 to accomplish further tasks or functions unrelated to the sensing of liquid level within the tank. Thus, the present invention is not limited to a module for sensing properties of the fluid but may include other modules that have various operations or functions indirectly associated with the fluid and/or independent of the fluid altogether.

Moreover, the cover associated with the chamber of the mounting head can be configured differently for each type of module to be installed for the particular application or applications desired. For example, the cover can be configured with a hose barb fitting, a wire or wire harness pass-through connector for electrical wires, a radio frequency antenna for transmitting and/or receiving information, and so on. In addition, although the cover has been shown as being installed after the module 100 is inserted into the chamber 130, and in accordance with a further embodiment of the invention, the cover can be provided with the module, either connected thereto or integrally formed therewith prior to installation on the mounting head 14, so that a particular cover configuration matches with a particular module configuration. The connection portion of each cover is preferably similar to thereby connect with the connection portion of the chamber or mounting head so that different modules with different configurations are interchangeable. In this manner, the need to keep track of separate cover configurations for different modules is eliminated.

Referring now to FIGS. 14 to 20, a liquid level transducer or apparatus 310 in accordance with a further exemplary embodiment of the invention is illustrated. As with the previous embodiment, the liquid level transducer 310 preferably extends into a container or tank (not shown), such as a fuel tank, oil reservoir, radiator, brake fluid chamber, or any other container for holding and/or transporting a liquid (not shown).

Although the transducer 310 is shown in the drawings with a vertical orientation, it will be understood that the transducer 310 can be configured for mounting in a horizontal orientation or any other suitable angle or orientation, without departing from the spirit and scope of the invention, such angle or orientation being dependent at least partially upon space constraints as dictated by the structure of the vehicle, machine, etc., with respect to the tank and/or the particular shape and mounting requirements of the tank.

The transducer 310 preferably includes a mounting head 314 for connection to a wall of the tank (not shown) and an elongate probe assembly 312 extending downwardly from the mounting head 314 for sensing a level of liquid within the tank. A housing 316 is preferably integrally formed with the mounting head 314 and extends downwardly therefrom to protrude into the inner space of the tank. However, it will be understood that the housing can protrude upwardly, e.g. away from the tank, without departing from the spirit and scope of the invention.

Figure 16:
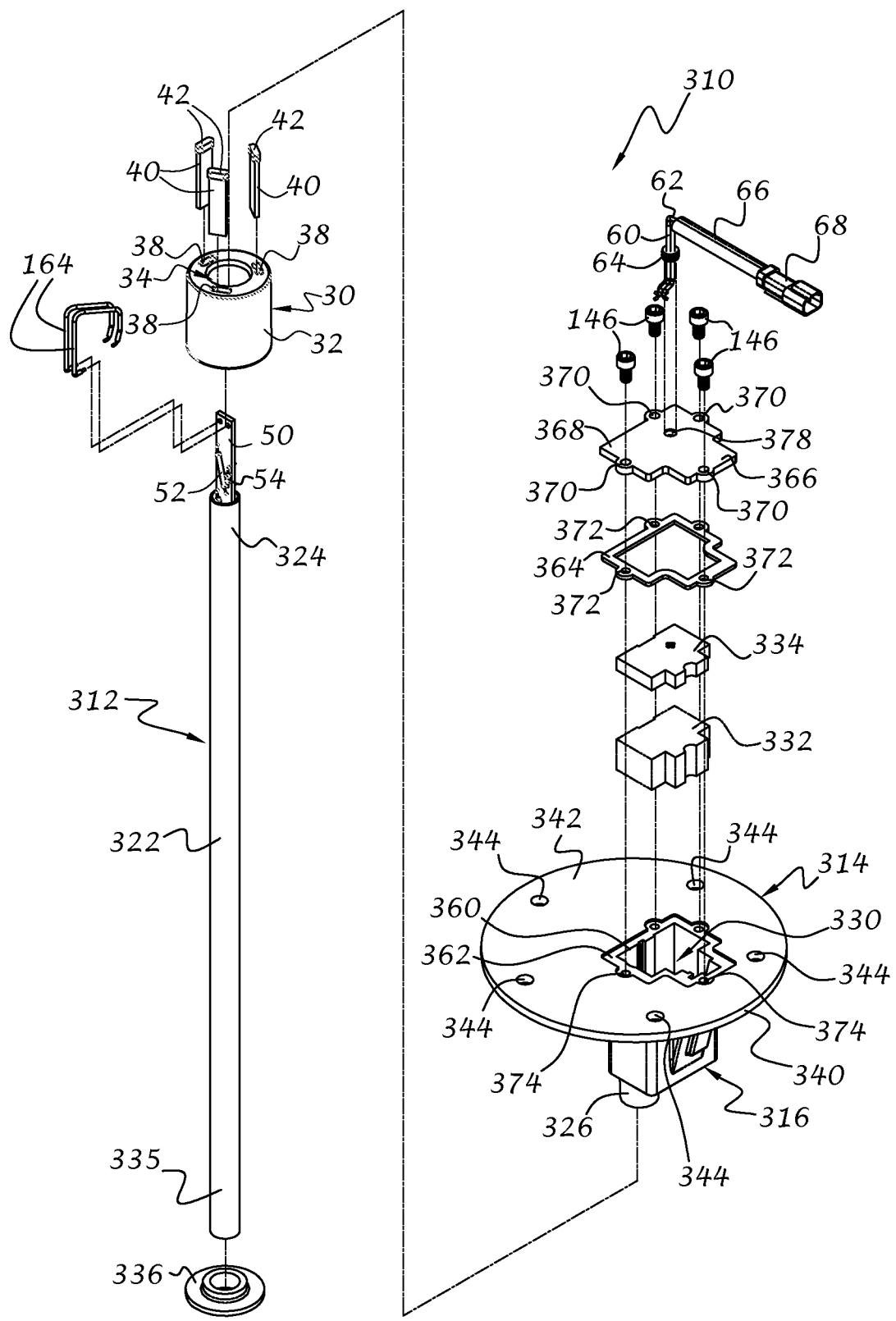
FIG. 16 is a top right-front exploded isometric view thereof.

As best shown in FIGS. 16, 18 and 20, the probe assembly 312 is configured to sense liquid level in a linear direction and can comprise similar structure or elements as the probe assembly 12 of the previous embodiment and is therefore designated with like numerals. Accordingly, the probe assembly 312 includes an outer sensor tube 322 with an upper end 324 that is press-fit into a collar 326 extending downwardly from the housing 316. A passageway 328 is defined by the collar 326 and, depending on the type of modules or devices, designated by numerals 332 and 334 in FIGS. 16 and 20 for example, can either be in fluid communication with an interior space or chamber 330 of the housing 316 or sealed from the chamber 330. A lower end 335 of the sensor tube 322 is press-fit into a lower support flange 336, which is generally annular in shape. It will be understood that the sensor tube 322 can be connected to the mounting head 314 and/or lower support flange 336 through other well-known connection means depending on the type of material used for the mounting head 314 and/or the sensor tube 322, such as surface welding (when both components are constructed of metal), adhesive bonding, mechanical fastening including threading or clamping, ultrasonic welding (when both components are constructed of plastic), and so on, without departing from the spirit and scope of the invention.

As with the previous embodiment, the probe assembly 12 includes a sensor board 50, preferably in the form of a printed circuit board (PCB), which is located in the sensor tube 322 and extends along a substantial length thereof. One or more electronic sensors 52 are located on the PCB and are responsive to one or more of the actuators 40 associated with the float 30 for indicating a change in liquid level upon the change in state of at least one of the sensors 52. The sensors 52 can comprise normally-open reed switches positioned along the length of the PCB 50 in series with a plurality of resistors 54 (FIGS. 16 and 20) for creating a liquid level signal, in conjunction with the resistors 54, as the float rides along the sensor tube 18 in response to a change in liquid level within the tank and thus a change in magnetic field at one or more sensor 52 locations. It will be understood that the sensors 52 can comprise normally closed reed switches. A controller, such as a microcontroller 325 (FIG. 18) and other supporting circuitry can be provided on the PCB 50 or associated therewith for further processing the signals from the electronic sensors as well as communicating the signals via hard-wired cable connections and/or via wireless transmission.

It will be further understood that other magnetic sensing devices can be used without departing from the spirit and scope of the invention. For example, other devices can include, but are not limited to, one or more solid state magnetic flux field sensors connected to the sensor board 50, Hall effect sensors, magnetoresistive (MR) sensors, anisotropic MR (AMR) sensors, giant magnetoresistance (GMR) sensors, solid state Micro-Electro-Mechanical Systems (MEMS), and magnetic switches. With the use of magnetic flux field or Hall effect sensors, a single sensor may be sufficient to determine the position of the magnet and thus the level of liquid within the tank depending on its length. Where the measurement length is too long for a single flux field sensor, a sufficient number of sensors placed at predetermined positions along the sensor board or on the surface of the sensor tube 322 itself can be used. In addition, when using a sensor that changes state in the presence and/or absence of a magnetic field, the magnets need not be arranged circumferentially about the float 30 as shown, nor is it an absolute requirement that three magnets be used, since one or more magnets may be adequate depending on the sensing technology used. Thus, the present invention is therefore adaptable to a wide variety of liquid level sensing technologies.

Moreover, other types of sensors that change in an electronically measurable manner in response to the proximity, presence, and/or absence of one or more actuators can be used, including for example nonmagnetic sensing technologies such as proximity detectors using capacitance, optical, or other measurement technologies, and so on. Likewise, the actuator can be in the form of one or more LED's, optical fibers, reflectors, as well as other light sources, and/or other contactless actuator/sensor arrangements to remotely change the electrical state of one or more sensor elements. In the event that optical sensors are used, the sensor tube 322 can be formed of a material that is translucent or transparent to the wavelength of the light source so that the sensor elements can readily detect movement of the light source in response to float movement as the liquid level in the container rises and falls.

Furthermore, other liquid level measurement technologies can be used for such as resistance cards and wiper arms, resistance wires or thick film devices that utilize the fluid as a heat sink to determine liquid level, capacitance or impedance measurement technologies where the liquid being measured functions as a dielectric or insulator, current flow, frequency, tuning forks, strain gauges, ultrasonic or other time domain devices, and so on.

Referring again to FIGS. 14-20, the mounting head 314 preferably includes a body 340 with a circular plate-shaped mounting flange 342 having the housing 316 formed therein. Mounting apertures 344 extend axially through the mounting flange 342 for mounting the transducer 310 to the wall of a tank (not shown) or the like. The mounting apertures 310 are adapted to receive threaded studs (not shown) extending outwardly from the tank wall in a well-known manner and as previously described, for connecting the transducer 310 to the tank. It will be understood that the tank-mounted studs can be replaced with screws or bolts or the like, that extend through the mounting apertures and thread into threaded apertures (not shown) in the tank wall. Other means for mounting the transducer 310 to the tank can be used without departing from the spirit and scope of the invention.

Moreover, it will be understood that the mounting head 314 is not limited to a flange mounting arrangement as shown, as other means for mounting the liquid level transducer 310 to a tank or other container can be used, including NPT type threads, clamping, welding, and so on, without departing from the spirit and scope of the invention. It will be further understood that the mounting head can be constructed of metal, such as brass, aluminum, stainless steel, and so on, or other materials such as plastic or ceramic.

Figure 14:
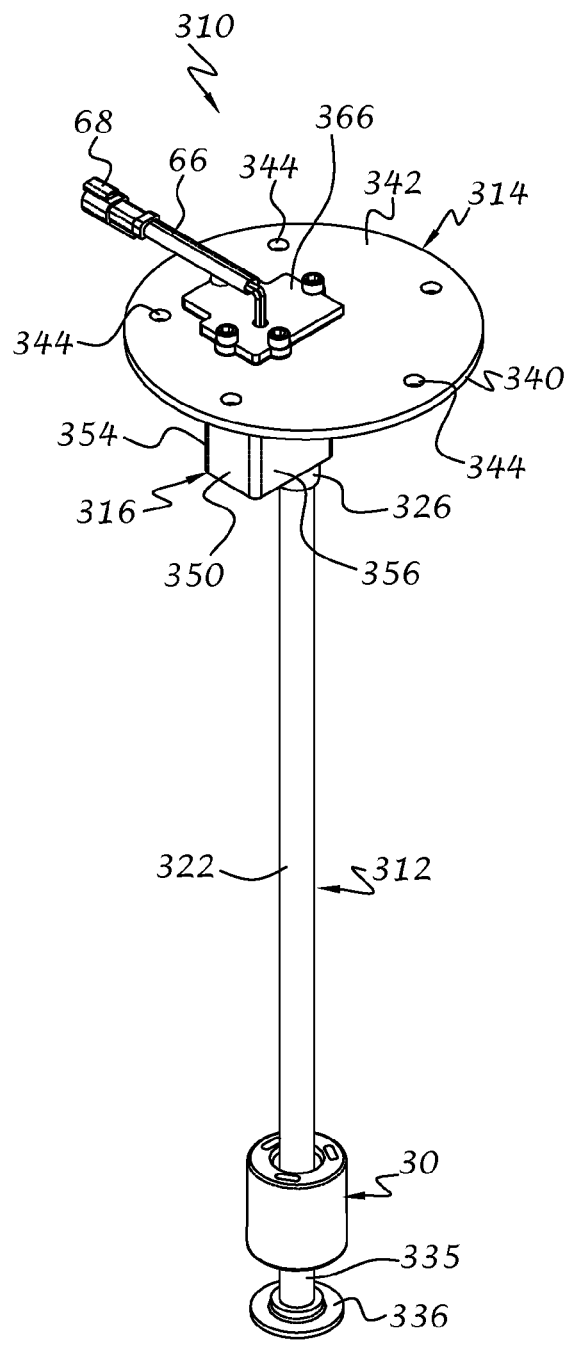
FIG. 14 is a top left-rear isometric view of a liquid level transducer in accordance with a further exemplary embodiment of the invention.
Figure 15:
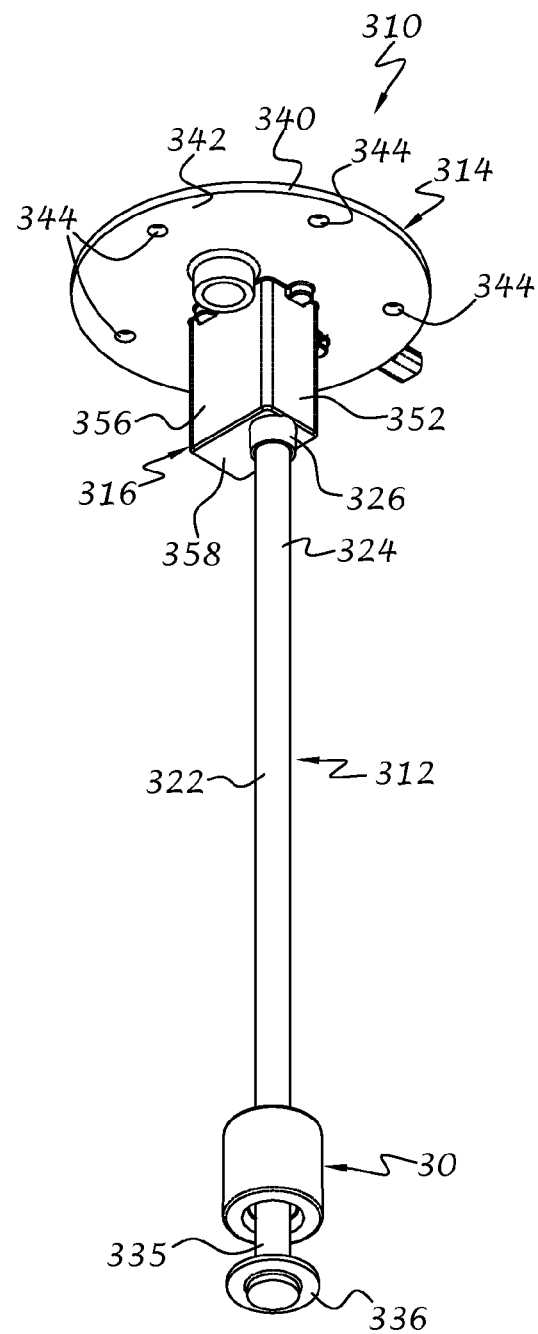
FIG. 15 is a bottom right-rear isometric view thereof.

As best shown in FIGS. 14 and 15, the housing 316 includes spaced upright side walls 350 and 352, spaced upright front and rear walls 354 and 356 extending between the side walls, and a bottom wall 358 extending between the upright walls. The upright walls 350, 352, 354, and 356 are preferably integrally formed with the body 340 and extend downwardly therefrom to define the hollow interior space or chamber 330 (FIG. 16).

As best shown in FIG. 16, an access opening 360 is formed in the body 340 coincident with the housing 316. A depression 362 is formed around the periphery of the opening 360 for receiving a seal or gasket 364. A top plate or cover 366 is removably connected to the mounting head 314 and fits over the access opening 360 to enclose the chamber 330 and its contents. To that end, the cover 366 can include a body or plate 368 with an outer periphery similar to the outer periphery of the access opening 360. Mounting apertures 370 are formed in the body 368 for receiving fasteners 146 that also extend through apertures 372 in the gasket 364 and thread into apertures 374 in the mounting head 314 to removably connect the cover 366 to the mounting head 314 with the gasket 364 sandwiched therebetween and thereby seal the chamber 330 from the outside environment.

An opening 378 is formed in the cover 366 for receiving the wire grommet 64 associated with the elongate probe assembly 312 for measuring liquid level as well as accomplishing other operations or functions associated with one or more modules 332, 334 for connecting to further electronics, such as but not limited to, a processor, display, transmitter, and so on, associated with the vehicle or equipment for relaying information about the fluid being measured to a user and/or control system for controlling or metering distribution of the liquid within the tank, monitoring the quality and/or composition of the liquid, alerting an operator or down line system when the tank has been filled with incorrect liquid for preventing damage to expensive components such as a catalytic converter when the tank holds a quantity of DEF fluid or the like, to control operation of the vehicle or equipment in the event that the liquid does not meet minimal quality and/or composition standards or requirements, and so on. In the event that the sensor module 100 comprises one or more filters for removing contaminants from the liquid as it exits the tank, the information can also include filter efficiency, differential pressure across the filter for determining when it should be replaced, unauthorized tampering or theft of the module 332, 334 or transducer 310, detection of fluid leaks or improper fluid within the tank, detection of vehicle tilt for correcting the level of fluid in the tank, fluid flow through the module for metering the quantity of fluid that may be transferred to another portion of the vehicle or machine, pressure and/or temperature of the fluid within the module and/or the tank, and so on, for additional display and/or processing with one or more control systems associated with the vehicle or machine. Such information can be sent to the control system via hardwire connection or wireless transmission of data from the transducer 10 via radio frequency transmitters, receivers and/or transceivers, RFID devices, and so on. Accordingly, it is contemplated that the modules 332 and/or 334 can include any apparatus, assembly, sensor, or device for measuring and/or controlling fluid properties or parameters, liquid level variations due to tilt, fluid sloshing, temperature and pressure fluctuations, and so on, that can be installed and removed separately and independently from the function of the liquid level sensing portion of the transducer 10.

As in the previous embodiment, the modules 330 and/or 332 are removably connected to the mounting head 314 of the transducer 310. The modules 330 and 332 can operate independently of the liquid level measurement system previously described, wherein the presence or absence of the modules does not affect liquid level measurement. Likewise, the absence of the liquid level measurement system does not affect the function(s) associated with the module(s).

As with the previous embodiment, the modules and/or devices associated with the modules can operate together or independently. It will be understood that the modules and/or devices can include any technology that determines fluid quality and/or composition, any device or apparatus that modifies the fluid including, but not limited to, one or more seals, filters for removing contaminants from the fluid, pumps, mixing chambers, metering valves or flow regulators.

The module(s) can also include one or more devices that would be useful for processing liquid level signals, such as one or more tilt sensors or acceleration sensors, vapor sensors, pressure sensors, transmitters, receivers, transceivers, and RFID devices for wirelessly communicating signals associated with the transducer 310 and detecting theft of the vehicle, equipment and/or transducer, an alarm for indicating tampering, theft, improper liquid within the tank, and so on.

The modules can also include devices for generating power through vehicle or equipment vibration, heat generation, and so on. Devices for conditioning the output signals can also be provided with one or more of the modules, power generating devices, different signal conditioning modules for selecting predefined output signals required by the vehicle or equipment associated with the transducer indicative of liquid level or other parameters of the liquid, tank, transducer, environmental conditions, and so on. For example, one vehicle may require a voltage output between 0 and 12 volts, to drive a fuel gauge between empty and full conditions of the tank, while another vehicle may require a voltage output of 0 to 5 volts. Other systems may require current output, pulse-width modulation, as well as other predefined signal output ranges and/or parameters. Accordingly, different modules can be selected and readily replaced or exchanged for other modules of similar or different functions to thereby provide a liquid level transducer that is adaptable to a wide variety of functions and capabilities depending on the particular needs of the vehicle or equipment with which the transducer is associated.

Although a particular shape of the mounting head, including the integral chamber, is shown, it will be understood that the mounting head is not limited to a single chamber or chambers having a particular shape. For example, one or more chambers integral to the mounting head can be circular with a circular cover or plate or of any other suitable shape that can be installed and removed for replacing one or more modules and/or one or more devices associated with the modules, The cover or plate can be configured for installation and removal for example by twisting, snap-fit engagement of the components, bolting, clamping including over-center clamp mechanisms, and so on.

Moreover, the cover associated with the chamber of the mounting head can be configured differently for each type of module to be installed for the particular application or applications desired. For example, the cover can be configured with a hose barb fitting, a wire or wire harness pass-through connector for electrical wires, a radio frequency antenna or RFID device for transmitting and/or receiving information, and so on. In addition, although the cover has been shown as being installed after the module is inserted into the chamber, and in accordance with a further embodiment of the invention, the cover can be provided with the module, either connected thereto or integrally formed therewith, prior to installation on the mounting head 314, so that a particular cover configuration matches with a particular module configuration. The connection portion of each cover is preferably similar to thereby connect with the connection portion of the chamber or mounting head so that different modules with different configurations are interchangeable. In this manner, the need to keep track of separate cover configurations for different modules is eliminated.

It will be understood that the term "preferably" as used throughout the specification refers to one or more exemplary embodiments of the invention and therefore is not to be interpreted in any limiting sense.

It will be further understood that the term "connect" and its derivatives refers to two or more parts capable of being attached together either directly or indirectly through one or more intermediate members. In addition, terms of orientation and/or position as may be used throughout the specification denote relative, rather than absolute orientations and/or positions.

It will be appreciated by those skilled in the art that changes could be made to the embodiments described above without departing from the broad inventive concept thereof. By way of example, The mounting head referred to throughout the specification can be used alone or in conjunction with a liquid withdrawal and return system for removing and returning liquid to the tank, and can also be associated with a liquid level transducer with sensing features for determining the level of liquid within the tank, as well as with a heat transfer system for warming the contents of the tank. The mounting had can also be in the form of a gauge head supporting an indicator or electronic device for communication information about the fluid to the user or system associated with the vehicle or machine connected to the tank. It is understood, therefore, that the invention is not limited to the particular embodiments disclosed, but is intended to cover all modifications within the spirit and scope of the present invention as defined by the appended claims.

What is claimed is:

1. An apparatus for determining at least first and second properties of a fluid associated with a tank, the apparatus comprising:
   a mounting head adapted for connection to the tank;
   a housing extending from the mounting head;
   a chamber located within the housing adapted to receive the fluid associated with the tank; and
   a module locatable in the chamber, the module being configured for enhancing operation of the apparatus when located in the chamber;
   wherein the module is insertable into the chamber and removable from the chamber without affecting determination of the second property of the fluid.

2. An apparatus according to claim 1, wherein the module comprises a sensor module for determining the first property of the fluid comprising at least one of fluid quality and fluid composition, and wherein the second property comprises a fluid level within the tank.

3. An apparatus according to claim 1, and further comprising a cover connectable to the housing for enclosing the chamber, the cover being removable to allow removal and installation of the module, and being operable to allow passage of fluid between the tank and a remote location associated with the vehicle or equipment when the chamber is void of the module.

4. An apparatus according to claim 3, and further comprising:
   a tube associated with the housing for withdrawing fluid from the tank;
   a hose connector associated with the cover in fluid communication with the chamber for transferring fluid from the tank to a distal location;
   wherein fluid is withdrawn from the tank, through the chamber, and through the hose connector independent of the presence and absence of the module within the chamber.

5. An apparatus according to claim 4, wherein the module comprises at least one device for performing at least one operation associated with the apparatus, the at least one device being selected from the group comprising: fluid quality sensors, fluid composition sensors, pressure sensors, vapor sensors, power generating devices, tilt sensors, acceleration sensors, transmitters, receivers, transceivers, RFID functions, theft alert, and signal conditioning for outputting a set of preselected signal parameters.

6. An apparatus according to claim 5, wherein the at least one device comprises a first device for determining the first property of the fluid including determining at least one of fluid quality and fluid composition.

7. An apparatus according to claim 6, wherein the first device comprises an optical sensor having a prism with a measurement surface in contact with the fluid, a light source for directing radiant energy toward the measurement surface, and an optical sensor for receiving reflected and/or refracted radiant energy from the measurement surface.

8. An apparatus according to claim 7, wherein the optical sensor comprises a two-dimensional image sensor with a plurality of pixels.

9. An apparatus according to claim 7, and further comprising a second device for determining a further property of the fluid.

10. An apparatus according to claim 9, wherein the second device comprises an impedance sensor for determining at least one of a capacitance, resistance, and inductance of the fluid.

11. An apparatus according to claim 1, wherein the module comprises at least one device for performing at least one operation associated with the apparatus, the at least one device being selected from the group comprising: fluid quality sensors, fluid composition sensors, pressure sensors, vapor sensors, power generating devices, tilt sensors, acceleration sensors, transmitters, receivers, transceivers, RFID functions, theft alert, and signal conditioning for outputting a set of preselected signal parameters.

12. An apparatus according to claim 11, and further comprising a plurality of interchangeable modules for installation in the chamber, each module comprising at least one device having a different operation such that each module performs a different function associated with the apparatus, each device being selected from the group comprising: fluid quality sensors, fluid composition sensors, pressure sensors, vapor sensors, power generating devices, tilt sensors, acceleration sensors, transmitters, receivers, transceivers, RFID functions, theft alert, and signal conditioning for outputting a set of preselected signal parameters.

13. An apparatus according to claim 1, and further comprising a plurality of interchangeable modules for installation in the chamber, each module comprising at least one device having a different operation such that each module performs a different function associated with the apparatus, each device being selected from the group comprising: fluid quality sensors, fluid composition sensors, pressure sensors, vapor sensors, power generating devices, tilt sensors, acceleration sensors, transmitters, receivers, transceivers, RFID functions, theft alert, and signal conditioning for outputting a set of preselected signal parameters.

14. An apparatus for determining at least first and second properties of fluid in a tank, the apparatus comprising:
a mounting head adapted for connection to the tank;
a sensor probe extending from the mounting head for determining the first fluid property comprising a level of fluid in the tank;
a housing extending from the mounting head;
a chamber located within the housing adapted to receive the fluid associated with the tank; and
a sensor module locatable in the chamber for determining the second property of the fluid;
wherein the sensor module is insertable and removable from the chamber without affecting determination of the level of fluid within the tank.

15. An apparatus according to claim 14, and further comprising a cover connectable to the housing for enclosing the chamber, the cover being removable to allow removal and installation of the sensor module, and being operable to allow passage of fluid between the tank and a remote location when the chamber is void of the sensor module.

16. An apparatus according to claim 14, wherein the sensor module comprises at least one device for performing at least one operation associated with the apparatus, the at least one device being selected from the group comprising: fluid quality sensors, fluid composition sensors, pressure sensors, vapor sensors, power generating devices, tilt sensors, acceleration sensors, transmitters, receivers, transceivers, RFID functions, theft alert, and signal conditioning for outputting a set of preselected signal parameters.

17. An apparatus according to claim 16, wherein the at least one device comprises a first device for determining the second property of the fluid including determining at least one of fluid quality and fluid composition.

18. An apparatus according to claim 17, wherein the first device comprises an optical sensor having a prism with a measurement surface in contact with the fluid, a light source for directing radiant energy toward the measurement surface, and an optical sensor for receiving reflected and/or refracted radiant energy from the measurement surface.

19. An apparatus according to claim 18, wherein the at least one device comprises a second device for determining a third property of the fluid.

20. An apparatus according to claim 19, wherein the second device comprises an impedance sensor for determining at least one of a capacitance, resistance, and inductance of the fluid.

21. An apparatus according to claim 14, and further comprising a plurality of interchangeable modules for installation in the chamber, each module comprising at least one device having a different operation such that each module performs a different function associated with the apparatus, each device being selected from the group comprising: fluid quality sensors, fluid composition sensors, pressure sensors, vapor sensors, power generating devices, tilt sensors, acceleration sensors, transmitters, receivers, transceivers, RFID functions, theft alert, and signal conditioning for outputting a set of preselected signal parameters.

22. A method for using a liquid level transducer, the method comprising:
providing a liquid level transducer with a mounting head for connection to a tank and a sensor extending therefrom for measuring a level of liquid within the tank;
providing a chamber in the mounting head for fluid communication between the tank and a distal location to withdraw liquid from or return liquid to the tank; and
providing a module for installation in the chamber for enhancing operation of the liquid level transducer, the module being operable to perform at least one function of a plurality of functions selected from the group comprising: measuring a quality of the liquid, measuring a composition of the liquid, measuring a pressure in the chamber, detecting the presence of vapor within the chamber, generating power for operating the transducer, determining a tilt or acceleration of the transducer, alerting unauthorized use or removal of the transducer, outputting a signal indicative of liquid level in accordance with predetermined parameters, performing RFID functions, and outputting a set of preselected signal parameters.

23. A method according to claim 22, wherein the step of providing a module comprises providing a plurality of interchangeable modules, with each module having one or more operations different from the other modules.

24. A method according to claim 23, and further comprising removing one of the modules from the chamber and installing another of the modules therein.

25. A method according to claim 22, wherein the module is operable to optically measure a first property of the fluid dependent on a refractive index thereof.

26. A method according to claim 22, wherein the module is operable to measure an impedance of the fluid, including at least one of a fluid capacitance, resistance, and inductance.

* * * * *